(12) United States Patent
Melosh et al.

(10) Patent No.: US 11,149,266 B2
(45) Date of Patent: Oct. 19, 2021

(54) METHODS OF NON-DESTRUCTIVE NANOSTRAW INTRACELLULAR SAMPLING FOR LONGITUDINAL CELL MONITORING

(71) Applicant: The Board of Trustees of the Leland Stanford Junior University, Stanford, CA (US)

(72) Inventors: Nicholas A. Melosh, Menlo Park, CA (US); Yuhong Cao, Palo Alto, CA (US); Karl Martin Hjort, Stanford, CA (US); Amanda Jonsson, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 250 days.

(21) Appl. No.: 16/332,684

(22) PCT Filed: Sep. 13, 2017

(86) PCT No.: PCT/US2017/051392
§ 371 (c)(1),
(2) Date: Mar. 12, 2019

(87) PCT Pub. No.: WO2018/053020
PCT Pub. Date: Mar. 22, 2018

(65) Prior Publication Data
US 2019/0359974 A1 Nov. 28, 2019

Related U.S. Application Data

(60) Provisional application No. 62/394,089, filed on Sep. 13, 2016.

(51) Int. Cl.
*C12M 1/26* (2006.01)
*C12N 15/10* (2006.01)
(Continued)

(52) U.S. Cl.
CPC ........ *C12N 15/1003* (2013.01); *C12M 33/04* (2013.01); *C12M 35/02* (2013.01);
(Continued)

(58) Field of Classification Search
None
See application file for complete search history.

(56) References Cited

U.S. PATENT DOCUMENTS 6,368,851 B1   4/2002   Baumann et al.
7,152,616 B2   12/2006  Zucchelli et al.
(Continued)

FOREIGN PATENT DOCUMENTS

CN   1286716 C     11/2006
CN   102656260 A   9/2012
(Continued)

OTHER PUBLICATIONS

Actis et al., ACS Nano. 8(1): 546-553 (2014).*
(Continued)

*Primary Examiner* — Erin M. Bowers
(74) *Attorney, Agent, or Firm* — Shay Glenn LLP

(57) ABSTRACT

Methods and apparatuses to non-destructively and periodically sample a small quantity of intracellular proteins and mRNA from the same single cell or cells for an extended period of time. Specifically, describe herein are non-perturbative methods for time-resolved, longitudinal extraction and quantitative measurement of intracellular proteins and nucleic acids from a variety of cell types using systems including nanostraws.

14 Claims, 15 Drawing Sheets

(51) Int. Cl.

| | |
|---|---|
| C12M 1/42 | (2006.01) |
| C12M 1/34 | (2006.01) |
| C12N 13/00 | (2006.01) |
| C12Q 1/24 | (2006.01) |
| B82Y 5/00 | (2011.01) |
| B82Y 15/00 | (2011.01) |
| B82Y 40/00 | (2011.01) |

(52) U.S. Cl.
CPC ............ *C12M 41/38* (2013.01); *C12N 13/00* (2013.01); *C12Q 1/24* (2013.01); *B82Y 5/00* (2013.01); *B82Y 15/00* (2013.01); *B82Y 40/00* (2013.01); *C12Q 2523/307* (2013.01)

(56) References Cited

U.S. PATENT DOCUMENTS

| | | |
|---|---|---|
| 7,160,532 B2 | 1/2007 | Liu et al. |
| 8,808,516 B2 | 8/2014 | Melosh et al. |
| 9,266,725 B2 | 2/2016 | Vandersarl et al. |
| 9,304,132 B2 | 4/2016 | Park et al. |
| 9,856,448 B2 | 1/2018 | Melosh et al. |
| 10,150,947 B2 | 12/2018 | Vandersarl et al. |
| 2004/0182707 A1 | 9/2004 | Jardemark et al. |
| 2006/0213259 A1 | 9/2006 | Prinz et al. |
| 2007/0100086 A1 | 5/2007 | Hong et al. |
| 2008/0302960 A1 | 12/2008 | Meister et al. |
| 2009/0220561 A1 | 9/2009 | Jin et al. |
| 2010/0035322 A1 | 2/2010 | Raffa et al. |
| 2010/0140111 A1 | 6/2010 | Gimsa et al. |
| 2010/0215724 A1 | 8/2010 | Prakash et al. |
| 2011/0168968 A1 | 7/2011 | Yang et al. |
| 2011/0208031 A1 | 8/2011 | Wolfe et al. |
| 2012/0040370 A1 | 2/2012 | Orwar et al. |
| 2012/0225435 A1 | 9/2012 | Seger et al. |
| 2012/0264108 A1 | 10/2012 | Chen et al. |
| 2013/0118621 A1 | 5/2013 | Weber et al. |
| 2014/0342445 A1 | 11/2014 | Ingber et al. |
| 2015/0197807 A1 | 7/2015 | Park et al. |
| 2016/0032275 A1 | 2/2016 | Actis et al. |
| 2019/0024122 A1 | 1/2019 | Hjort et al. |
| 2019/0119629 A1 | 4/2019 | Vandersarl et al. |
| 2019/0365803 A1 | 12/2019 | Melosh et al. |
| 2019/0367861 A1 | 12/2019 | Swoboda et al. |

FOREIGN PATENT DOCUMENTS

| | | |
|---|---|---|
| JP | 11346764 A | 12/1999 |
| JP | 2003501639 A | 1/2003 |
| JP | 2003505073 A | 2/2003 |
| JP | 2009541198 A | 11/2009 |
| WO | WO2002/058847 A2 | 8/2002 |
| WO | WO2009/063776 A1 | 3/2011 |
| WO | WO2017/027549 A1 | 2/2017 |
| WO | WO2017/214541 A1 | 12/2017 |
| WO | WO2018/053020 A1 | 3/2018 |
| WO | WO2019/018415 A1 | 1/2019 |

OTHER PUBLICATIONS

Cao et al.; Non destructive nanostraw intracellular sampling for longitudinal call monitoring; Proceedings of the National Academy of Sciences; 114(10); pp. E1866-E1874; XP002797487; Mar. 1, 2017.

Liu et al.; Voyage inside the cell: Microsystems and nanoengineering for intracellular measurement and manipulation, Microsystems & Nanoengineering; 1(1); XP055666437; DOI: 10.1038/micronano.2015.20: Sep. 14, 2015.

Baek et al., Gene transfection for stem cell therapy; Current Stem Cell Reports; 2(1); pp. 52-61; Jan. 27, 2016.

Schmiderer et al.: Efficient and nontoxic biomolecule delivery to primary human hernatopoietic stem cells using nanostraws; Proceedings of the National Academy of Sciences; 117(35); pp. 21267-21273; Sep. 2020.

Hjort et al.; U.S. Appl. No. 17/081,983 entitled "Apparatuses and methods using nanostraws to deliver biologically relevant cargo into non-adherent cells," filed Oct. 27, 2020.

Abhyankar et al.; Characterization of a membrane-based gradient generator for use in cell-signaling studies; Lab Chip; 6(3);389-393; Mar. 2006.

Actis et al.; Compartmental genomics in living cells revealed by single-cell nanobiopsy; ACS Nano; 8(1); pp. 546-553; Jan. 28, 2014.

Adler et al.; Emerging links between surface nanotechnology and endocytosis: impact on nonviral gene delivery; Nano Today; 5(6):553-569; Dec. 2010 (author manuscript, 15 pgs.).

Ainslie et al.; Microfabricated devices for enhanced bioadhesive drug-delivery: attachment to and small-molecule release through a cell monolayer under flow: Small; 5(24):2857-2863; Dec. 2009.

Almquist et al.; Fusion of biomimetic stealth probes into lipid bilayer cores; Proc Nati Acad Sci U S A.; 107(13):5815-5820; Mar. 2010.

Almquist et al.; Nanoscale patterning controls inorganic-membrane interface structure; Nanoscale; 3(2):391-400; Feb. 2011.

Bancroft et al.; Fluid flow increases mineralized matrix deposition in 3D perfusion culture of marrow stromal osteoblasts in a dose-dependent manner; PNAS; 99(20):12600-12605; Oct. 1, 2002.

Bernards et al.; Nanoscale porosity in polymer films: fabrication and therapeutic applications; Soft Matter; 6(8):1621-1631; Jan. 2010 (author manuscript, 13 pgs.).

Black et al.; Upregulation of a silent sodium channel after peripheral, not not central, nerve injury in DRG neurons; J Neurophysiol; 82(5); pp. 2776-2785; Nov. 1999.

Boyden; The chemotactic effect of mixtures of antibody and antigen on polymorphonuclear leucocytes; J Exp Med; 115;453-466; Mar. 1, 1962.

Cao et al.; Template-based synthesis of nanorods, nanowire and nanotube array; Adv Colloid Interface Sci; 136(1-2):45-64; Jan. 15, 2008.

Carter; Potent antibody therapeutics by design; Nat Rev Immunol; 6(5);343-57; May 2006.

Chen et al.; A cell nanoinjector based on carbon nanotubes; Proc Natl Acad Sci U S A.; 104(20):8218-8222; May 15, 2007.

Choi; A Cellular Trojan Horse for Delivery of Therapeutic Nanoparticles into Tumors. Nano Letters; 7(12), pp. 3759-3765; Dec. 2007.

Chu et al.; Electroporation for the efficient transfection of mammalian cells with DNA; Nucleic Acids Res.; 15(3):1311-1326; Feb. 11, 1987.

Das et al.; TiO2 nanotubes on Ti: influence of nanoscale morphology on bone cell-materials interaction; Journal of Biomedical Materials Research Part A; 90(1); pp. 225-237; Jun. 1, 1990.

Daub et al.; Ferromagnetic nanotubes by atomic layer deposition in anodic alumina membranes; J. Appl. Phys.; 101; 09J111 (4 pgs.); May 2007.

Dertinger et al.; Generation of Gradients Having Complex Shapes Using Microfluidic Networks; Anal Chem; 73:1240-1246; Feb. 16, 2001.

Diao et al.; A three-channel microfluidic device for generating static linear gradients and its application to the quantitative analysis of bacterial chemotaxis; Lab Chip; 6(3)361-389; Mar. 2006.

Dubey et al.; Intercellular nanotubes mediate bacterial communication; Cell; 144(4):590-600; Feb. 2011.

El-Ali et al.; Cells on Chips; Nature; 442(7101):403-411; Jul. 27, 2006.

Engler et al.; Matrix Elasticity Directs Stem Cell Lineage Specification; Cell; 126(4):677-689; Aug. 25, 2006.

Ertan et al.; Electrodeposition of nickel nanowires and nanotubes using various templates; Journal of Experimental Nanoscience; 3 (4); pp. 287-295; Dec. 2008.

Gasiorowski et al.; Alterations in gene expression of human vascular endothelial cells associated with nanotopographic cues; Biomaterials; 31(34):8882-8; Dec. 2010 (author manuscript, 15 pgs.).

Geldof; Nerve-growth-factor-dependent neurite outgrowth assay; a research model for chemotherapy-induced neuropathy; J Cancer Res Clin Oncol; 121(11):657-660; Feb. 1995.

(56) References Cited

OTHER PUBLICATIONS

Gheith et al; Stimulation of Neural Cells by Lateral Currents in Conductive Layer-by-Layer Films of Single-Walled Carbon Nanotubes; Adv Mater; 18(22):2975-2979; Nov. 2006.
Giancotti et al.; Integrin signaling; Science; 285(5434):1028-1032; Aug. 13, 1999.
Goetz et al; Computer simulations of bilayer membranes: Self-assembly and interfacial tension; J Chem Phys; 108(7):7397-7409; May 1, 1998.
Griffith et al.; Polymeric biomaterials; Acta Mater; 48(1):263-277; Jan. 1, 2000.
Hanna et al.; Direct cell reprogramming is a stochastic process amenable to acceleration; Nature;462(7273):595-601; Dec. 2009 (auhor manuscript, 17 pgs.).
Haydon et al.; Anaesthesia by the n-alkanes. A comparative study of nerve impulse blockage and the properties of black lipid bilayer membranes: BBA—Biomembranes: 470(1):17-34; Oct 3. 1977.
Haydon et al.; The molecular mechanisms of anaesthesia; Nature; 268:356-358; Jul. 28, 1977.
Heath et al.; Nanotechnology and cancer; Annu Rev Med; 59:251-65; Feb. 2008 (author manuscript, 16 pgs.).
James et al.; Patterned protein layers on solid substrates by thin stamp microcontact printing; Langmuir; 14(4); pp. 741-744; Jan. 1998.
Jeon et al.; Generation of Solution and Surface Gradients Using Microfluidic Systems; Langmuir; 16(22):8311-8316; Oct. 31, 2000.
Keenan et al.; Microfluidic jets for generating steady-state gradients of soluble molecules on open surfaces; Appl. Phys. Lett.; 89(11);114103-114103-3; Sep. 11, 2006.
Keenan et al.; Biomolecular gradients in cell culture systems; Lab Chip; 8(1):34-57; Jan. 2008.
Kim et al.; Interfacing Silicon Nanowires with Mammalian Cells; J Am Chem Soc; 129(23):7228-7229; Jun. 13, 2007.
Kinoshita; Electrochemical Uses of Carbon; Electrochem Encycl; pp. 11; Jan. 2001.
Knez et al.; Synthesis and Surface Engineering of Complex Nanostructures by Atomic Layer Deposition; Adv Mater; 19(21):3425-3437; Nov. 2007.
Kubota et al.; Role of laminin and basement membrane in the morphological differentiation of human endothelial cells into capillary-like structures; Journal of Cell Biology; 107; pp. 1589-1598; Oct. 1988.
Kumar et al.; The gap junction communication channel; Cell; 84(3):381-8; Feb. 1996.
Kwak et al.; Interfacing inorganic nanowire arrays and living cells for cellular function analysis; Small; 11(42); pp. 5600-5610; Nov. 11, 2015.
Langer; Drug delivery and targeting; Nature; 392(6679 Suppl):5-10.; Apr. 1998.
Langille et al.; Relationship between blood flow direction and endothelial cell orientation at arterial branch sites in rabbits and mice; Circ Res; 48(4):481-488; Apr. 1981.
Lee et al.; Hydrogels for tissue engineering; Chem Rev; 101(7):1869-1879; Jul. 2001.
Li et al.; Nanotube arrays in porous anodic alumina membranes; J. Mater. Sci. Tech.; 24(4); pp. 550-562; Jul. 2008.
Loh et al.; Nanofountain-probe-based high-resolution patterning and single-cell injection of functionalized nanodiamonds; Small; 5(14):1667-1674; Jul. 2009.
Luo et al.; Synthetic DNA delivery systems; Nat Biotechnol; 18(1);33-7; Jan. 2000.
Lutolf et al.; Synthetic biomaterials as instructive extracellular microenvironments for morphogenesis in tissue engineering; Nat Biotecnol; 23(1):47-55; Jan. 2005.
Malboubi et al.; Effects of the Surface Morphology of Pipette Tip on Giga-seal Formation. Engineering Letters; 17(4), p. 281; Nov. 2009.
Martin; Nanomaterials: a membrane-based synthetic approach; Science; 266 (5193):1961-6.; Dec. 1994.

McKnight et al.; Tracking gene expression after DNA delivery using spatially indexed nanofiber arrays; Nano Letters; 4(7); pp. 1213-1219; May 2004.
Michalet et al.; Quantum dots for live cells, in vivo imaging, and diagnostics; Science; 307(5709):538-44, Jan. 28, 2005 (author manuscript; 16 pgs.).
Oates et al.; Role of titanium surface topography and surface wettability on focal adhesion kinase mediated signaling in fibroblasts; Materials; 4(5); pp. 893-907; May 9, 2011.
Patel, et al.; Spatially controlled cell engineering on biodegradable polymer surfaces; FASEB J; 12(14):1447-1454; Nov. 1998.
Peng et al.; Whole genome expression analysis reveals differential effects of TiO2 nanotubes on vascular cells; Nano Letters; 10(1); pp. 143-148; Jan. 2010.
Persson et al.; Vertical Nanotubes Connected by a Subsurface Nanochannel; 14th Int'l Conference on Miniturized Systems fror Chemistry and Life Sciences; 1862-1864; Oct. 3-7, 2010.
Petronilli et al.; Transient and long-lasting openings of the mitochondrial permeability transition pore can be monitored directly in intact cells by changes in mitochondrial calcein fluorescence; Biophys J.; 76(2).725-34.; Feb. 1999.
Plath et al.; Progress in understanding reprogramming to the induced pluripotent state; Nat Rev Genet.; 12(4):253-265; Apr. 2011 (author manuscript, 26 pgs.).
Qi; Cell adhesion and spreading behavior on vertically aligned silicon nanowire arrays; ACS Appl Mater Interfaces; 1(1):30-4; Jan. 2009.
Ruoslahti; New perspectives in cell adhesion: RGD and integrins; Science; 238(4826):491-7; Oct. 1987.
Safran et al.; Database update: GeneCards version 3: the human gene integrator; Database (Oxford); vol. 2010 (baq020); 16 pgs.; Aug. 2010.
Saito; A Theoretical Study on the Diffusion Current at the Stationary Electrodes of Circular and Narrow Band Types; Rev Polarography; 15(6):177-187; Dec. 1968.
Sakiyama-Elbert et al.; Controlled release of nerve growth factor from a heparin-containing fibrin-based cell ingrowth matrix; J Control Release; 69(1):149-158; Oct. 3, 2000.
Scadden; The stem-cell niche as an entity of action; Nature; 441 (7097):1075-1079; Jun. 29, 2006.
Shalek et al.; Vertical silicon nanowires as a universal platform for delivering biomolecules into living cells; Proc Natl Acad Sci U S A.; 107(5):1870-1875; Feb. 2, 2010.
Sharei et al.; Ex Vivo Cytosolic Delivery of Functional Macromolecules to Immune Cells; PloS One; 10(4); e0118803, 12 pages; Jan. 7, 2015.
Shamloo et al.; Endothelial cell polarization and chemotaxis in a microfluidic device; Lab Chip; 8(8):1292-1299; Aug. 2008.
Sip et al.; Microfluidic transweil inserts for generation of tissue culture-friendly gradients in wall plates; Lab on a Chip, 14(2); pp. 302-314; (year of pub. sufficiently earlier than effective US filing date and any foreign priority date); 2014.
Susin et al.; Molecular characterization of mitochondrial apoptosis-inducing factor; Nature; 397; pp. 441-446; Feb. 1999.
Tian et al.; Fabrication of high density metallic nanowires and nanotubes for cell culture studies; Microelectronic Eng; 88(8):1702-1706; Aug. 2011.
Tian et al.; Three-dimensional, flexible nanoscale field-effect transistors as localized bioprobes; Science;329(5993):830-4; Aug. 2010 (author manuscript, 11 pgs.).
Tiscornia et al.; A general method for gene knockdown in mice by using lentiviral vectors expressing small interfering RNA; Proc Natl Acad Sci U S A.; 100(4)1844-1848; Feb. 18, 2003.
Uhrich et al.; Polymer systems for controlled drug release; Chem Rev; 99(11):3181-3198; Nov. 10, 1999.
Vandersarl et al.; Nanostraws for direct fluidic intracellular access; Nano Letters; 12(8); pp. 3881-3886; Dec. 20, 2011.
Verma et al.; Gigaohm resistance membrane seals with stealth probe electrodes; Appl Phys Lett; 97(3):1-3; Jul. 2010.
Verma et al.; Surface-structure-regulated cell-membrane penetration by monolayer-protected nanoparticles; Nat Mater; 7(7):588-595; Jul. 2008 (Author Manuscript; pp. 15).

(56) References Cited

OTHER PUBLICATIONS

Walker et al.; Effects of flow and diffusion on chemotaxis studies in a microfabricated gradient generator; Lab Chip; 5(6):611-618; Jun. 2005 (Author Manuscript; pp. 18).

Wang et al.; Neural stimulation with a carbon nanotube microelectrode array; Nano Lett; 6(9):2043-2048; Sep. 2006.

Wang et al.; Shear stress induces endothelial differentiation from a murine embryonic mesenchymal progenitor cell line; Arterioscler Thromb Vasc Biol; 25(9):1817-1823; Sep. 2005.

Whitesides; The origins and the future of microfluidics; Nature; 442(7101):368-373; Jul. 27, 2006.

Wolfe et al.; U.S. Appl. No. 61/306,778 entitled "Neutral Particle Nanopatterning for Nonplanar Multimodal Neural Probes," filed Feb. 22, 2010.

Wu et al.; Generation of complex, static solution gradients in microfluidic channels; J Am Chem Soc; 128(13):4194-4195; Apr. 5, 2006.

Xiao et al.; Fabrication of Alumina Nanotubes and Nanowires by Etching Porous Alumina Membranes; Nano Lett; 2(11):1293-1297; Oct. 26, 2002.

Xie et al.; Vertical nanopillars for highly localized fluorescence imaging; Proc Natl Aced Sci U S A.; 108(10):3894-9; Mar. 2011.

Xie et al.; Mechanical model of vertical nanowire cell penetration; Nano Letters; 13(12); pp. 6002-6008; Nov. 20, 2013.

Xie et al.; Nanostraw-Electroportation System for Highly Efficient Intracellular Delivery and Transfection; ACS Nano; 7(5); pp. 4351-4358; Apr. 18, 2013.

Yang et al.; Semiconductor nanowire: What's Next?; Nano Letters; 10; pp. 1529-1536; May 2010.

Yu et al.; Diffusion dependent cell behavior in microenvironments; Lab Chip; 5(10):1089-1095; Oct. 2005.

Yu et al.; Nano Wheat Fields Prepared by Plasma-Etching Gold Nanowire-Containing Membranes; Nano Lett; 3(6);815-818; Mar. 20, 2003.

Zeck et al.; Noninvasive neuroelectronic interfacing with synaptically connected snail neurons immobilized on a semiconductor chip; Proc Natl Acad Sci U S A.; 98(18):10457-62; Aug. 2001.

Zicha et al.; A new direct-viewing chemotaxis chamber; J Cell Sci; 99(4);769-775; Aug. 1991.

Zigmond; Orientation chamber in chemotaxis; Methods Enzymol; 162:65-72; Oct. 12, 1988.

Chang et al.; Dielectrophoresis-assisted 3D nanoelectroporation for non-viral cell transfection in adoptive immunotherapy. Lab on a Chip. 15(15); pp. 3147-3153; Jun. 2015.

Chang et al.; Magnetic tweezers-based 3D microchannel electroporation for high-throughput gene transfection in living ceils; Small; 11(15); pp. 1818-1828; 20 pages (Author Manuscript); Apr. 2015.

\* cited by examiner

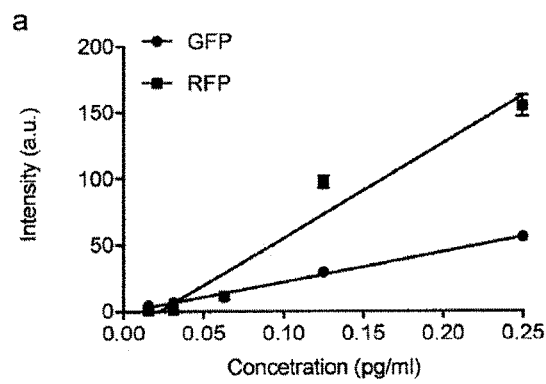
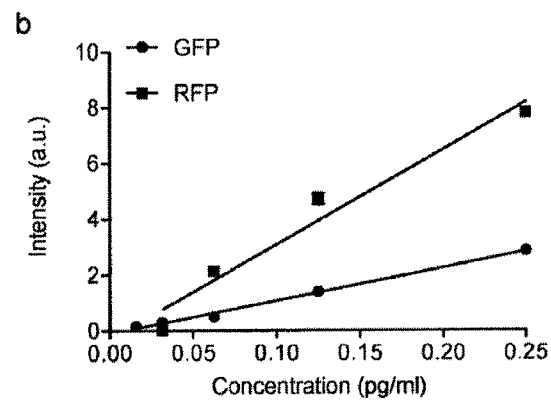
FIG. 11a                FIG. 11b
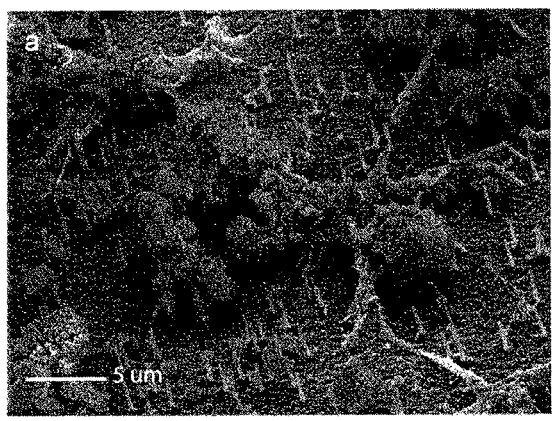
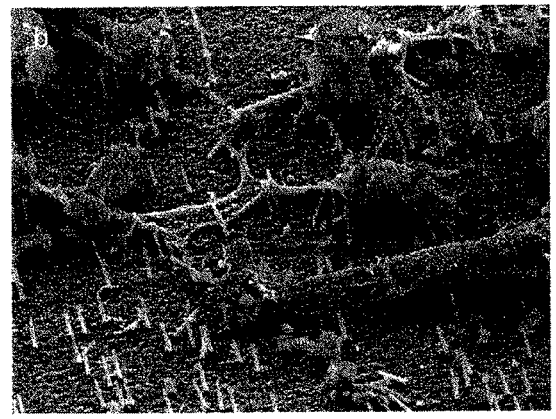
FIG. 12a                FIG. 12b

| Name | Length (nt) | Name | Length (nt) | Name | Length(nt) |
|---|---|---|---|---|---|
| ACTN1 | 3306 | LEFTY2 | 1230 | RYR2 | 16562 |
| ADRB1 | 2862 | MAPK14 | 1083 | SCN5A | 8343 |
| ATP2A2 | 4359 | MEF2C | 5915 | SCL2A4 | 3159 |
| BMP4 | 1774 | MYH6 | 351 | SMAD2 | 10428 |
| BMPR1A | 3631 | MYH7 | 6069 | TBX5 | 3828 |
| CASQ2 | 2716 | MYL2 | 630 | TGFB2 | 5882 |
| CSNK1A1 | 2100 | MYL7 | 830 | TGFBR2 | 4704 |
| FGF2 | 6774 | MYOCD | 3093 | TNNC1 | 705 |
| GAPDH | 1407 | NKX25 | 1669 | TNNI3 | 866 |
| GATA4 | 2662 | NODAL | 2086 | TNNT2 | 1307 |
| GJA1 | 3169 | NPPA | 858 | VCAM1 | 3220 |
| GRB2 | 3303 | PLN | 1742 | WNT1 | 2284 |
| HAND1 | 1749 | POU5F1 | 2075 | WNT3A | 2988 |
| HAND2 | 675 | PPARA | 1302 | ACTB | 1852 |
| HCN4 | 7245 | PPARGC1A | 6318 | GUSB | 2228 |
| KCNJ2 | 1622 | PRKAA1 | 5085 | HPRT1 | 1435 |

FIG. 16

METHODS OF NON-DESTRUCTIVE NANOSTRAW INTRACELLULAR SAMPLING FOR LONGITUDINAL CELL MONITORING

CROSS REFERENCE TO RELATED APPLICATIONS

This patent application claims priority to U.S. provisional patent application No. 62/394,089, filed on Sep. 13, 2016, and titled "METHODS OF NON-DESTRUCTIVE NANOSTRAW INTRACELLULAR SAMPLING FOR LONGITUDINAL CELL MONITORING". This patent application is herein incorporated by reference in its entirety.

STATEMENT AS TO FEDERALLY SPONSORED RESEARCH

This invention was made with Government support under contract HL133272 awarded by the National Institutes of Health and under contract 70NANB15H268 awarded by the National Institute of Standards and Technology. The Government has certain rights in the invention.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The present invention relates generally to methods for accessing and sampling from intracellular spaces, in particular methods for accessing and sampling from intracellular spaces using nanostraw systems.

BACKGROUND

Quantitative analyses of intracellular components, such as proteins and mRNA, may provide crucial information to decipher cellular behavior related to disease pathogenesis, cellular senescence, development and differentiation. Increasingly sensitive, and even single-cell, mRNA and protein detection methods have been developed, leading to new insights into cell function, phenotype heterogeneity, and noise in cellular systems. Although powerful, these methods are hampered by the need to lyse the cell to extract the intracellular contents, providing only a single snapshot in time without information about prior or future states. This is particularly problematic when studying dynamic transformations, including induced pluripotency and differentiation, or stochastic noise in gene expression at the single cell level. Phenotype heterogeneity and fluctuations in single cells imply that cells in parallel cultures are often not representative, highlighting the need for non-destructive sampling from the same set of cells repeatedly over time.

Although time-resolved, longitudinal monitoring of some cells (e.g., sampling the same population of cells periodically) has been possible to some extent with intracellular fluorescence techniques, these techniques typically do not allow ongoing sampling of otherwise unmarked cellular components. Such techniques typically require genetically encoded fluorescent protein (FP)-based biosensors to non-destructively follow intracellular enzymatic activity. In addition, it has monitoring of two to five species of proteins in living cells has been demonstrated using fluorescence resonance energy transfer (FRET) biosensors and bimolecular fluorescence complementation (BiFC), however, the number of intracellular targets is still limited due to spectral overlap. The presence of the FP label may also interfere with the function of the fused protein, and validating the specificity of the sensor is crucial. Further, the transfection of the FP gene is itself an intrusive process. Genetically encoded biosensors, such as quantum dot (QD) labeled antibodies and molecular beacons, are also used for intracellular detection, yet are challenging to deliver intracellularly, and perturbation of the cell due to the labeling methods and presence of label is still a significant concern. Overall, even with the availability of FP methods, longitudinal studies are relatively rare.

Nanotechnology provides an alternative approach by taking advantage of nanoscale dimensions to non-destructively introduce sensors into cells, or to extract small quantities of cellular contents. For example, a nanowire 'sandwich assay' has been proposed, in which ~100 nm diameter nanowires functionalized with antibodies penetrate the cell with limited toxicity to bind specific enzymes for extraction. Actis et al. (Actis, et al., Compartmental Genomics in Living Cells Revealed by Single-Cell Nanobiopsy, ACS Nano. 2014 Jan. 28; 8(1):546-553) demonstrated a 'nanobiopsy' which extracts fluid (e.g., approximated to be 50 fL) from the cytoplasm a single cell without cell cytotoxicity with around 70% success rate. Another nano-sampling approach have also been described using an AFM-based sampling platform with controlled pL volume extraction, followed by a single time-point mRNA analysis. This technique was found to be largely non-destructive, with 86% cell viability, demonstrating that cells may lose a fraction of their volume without apoptosis. Intracellular protein sampling was also possible using magnetized carbon nanotubes coated with poly-1-tyrosine to extract green fluorescent protein (GFP) from a cell culture, with better than 70% cell viability. These promising results indicate that insertion and sampling at a single time-point is possible. However, none of these approaches repeatedly sampled from the same set of cells to follow their expression over time, nor provided quantitative assessment of the measured quantities compared with the actual intracellular contents. Described herein are methods and apparatuses that may address the needs and problems mentioned above.

SUMMARY OF THE DISCLOSURE

Described herein are methods and apparatuses to non-destructively and periodically sample a small quantity of intracellular proteins and mRNA from the same single cell or cells for an extended period of time. Specifically, describe herein are non-perturbative methods for time-resolved, longitudinal extraction and quantitative measurement of intracellular proteins and nucleic acids from a variety of cell types using systems including nanostraws.

Here we report a non-perturbative method for time-resolved, longitudinal extraction and quantitative measurement of intracellular proteins and mRNA from a variety of cell types. Using these methods and apparatuses, cytosolic contents were repeatedly sampled from the same cell or population of cells for over 5 days through a cell culture substrate incorporating hollow nanostraws having an inner diameter of, e.g., between 20 and 1000 nm (e.g., between 20-900 nm, between 20-800 nm, between 20-700 nm, between 20-600 nm, between 20-500 nm, between 20-400 nm, between 20-300 nm, between 20-200 nm, etc.) and an outer diameter of between, e.g., 50 and 1500 nm (e.g., between 50-1400 nm, between 50-1300, between 50-1200 nm, between 50-1100 nm, between 50-1000 nm, between 50-900 nm, between 50-800 nm, between 50-700 nm, between 50-600 nm, between 50-500 nm, between 50-400 nm, between 50-300 nm, between 50-200 nm, etc.) within a defined sampling region. The techniques and apparatuses described herein may open, for a discrete time period, pores or gaps within the portion of the cell membrane over the contents may be extracted by a highly focused electroporation technique at the nanostraw distal opening in contact with the cell membrane, allowing diffusion of intracellular components (which may be driven by an applied electrical field) for sampling from the nanostraw.

Once extracted, the cellular contents may be analyzed with conventional methods, including fluorescence, enzymatic assays (ELISA), and quantitative real-time polymerase chain reaction (qPCR). This process is non-destructive, with >95% cell viability after sampling, enabling long-term analysis. Importantly, the measured quantities from the cell extract have been found to constitute a statistically significant representation of the actual contents within the cells. For example, as will be described herein, of 48 mRNA sequences analyzed from a population of human cardiomyocytes derived from pluripotent stem cells (hiPSC-CMs), 41 were accurately quantified. The methods and apparatuses described herein may sample from a select sub-population of cells within a larger culture, allowing native cell-to-cell contact and communication even during vigorous activity such as cardiomyocyte beating. These methods and apparatuses may be applied to both cell lines and primary cells (including, but not limited to the examples provided herein, e.g., Chinese hamster ovary cells, hiPSC-CMs, and human astrocytes derived in 3D cortical spheroids). By tracking the same cell or group of cells over time, these methods and apparatuses offer new avenues to understand dynamic cell behavior, including processes such as induced pluripotency and differentiation.

For example, described herein are methods of nondestructive sampling of intracellular sample material from within a cell. These methods may include sampling at a single time point or at multiple time points. For example, any of these methods may include: applying a voltage between an upper electrode and a lower electrode through a nanostraw to open one or more pores in a portion of the cell membrane extending over an opening of the nanostraw; capturing a sample material released from within the cell and into the nanostraw in a sample collector beneath the nanostraw; and stopping the application of voltage between the upper and lower electrodes and allowing the cell membrane to recover before more than 15% of the sample material within the cell is released.

Applying a voltage between an upper electrode and a lower electrode through a nanostraw to open one or more pores in a portion of the cell membrane extending over an opening of the nanostraw may include applying a pulsed (e.g., positive, negative, and/or biphasic) voltage pulses, or current pulses. The pulses may have a fixed or varying pulse width and pulse rate. The voltage may be applied for any appropriate duration. The voltage parameters, including the voltage duration, may be set by the cell size and type, and may be determined empirically, to prevent cell death. As described in greater detail herein, the applied voltage (including the pulse parameters) may be selected to prevent release, by diffusion and/or charge driven (e.g., electrophoresis) mobility. For example, applying may comprise applying a pulsed voltage of between 1 and 100 V between the upper electrode and the lower electrode through a nanostraw, e.g., having a pulse width of between about 10 microseconds (μs) and 50 milliseconds (ms) (e.g., such as between 10 μs and 10 ms, between 20 μs and 5 ms, between 20 μs and 1 ms, between 20 μs and 500 μs, etc.). The voltage may be applied for a duration that allows sample material to move out of the cell, through the temporary cell membrane opening and into the nanostraw, so that it may be captured by the sample collector.

Typically, the application of voltage to form openings in the cell membrane is stopped before more than 25% (e.g., more than 20%, more than 15%, more than 14%, more than 13%, more than 12%, more than 11%, more than 10%, more than 9%, more than 8%, more than 7%, more than 6%, more than 5%, etc.) of the sample material within the cell is released. Beyond this point, the cell may be more likely to die, and therefore it is beneficial to stop the application of voltage (and to allow the cell to recover). For example, the application of voltage may be stopped before more than 15% of the sample material within the cell is released through the opening(s) in the cell membrane. The amount of sample material released through the cell may be dependent on the strength of the applied electrical field (e.g., the applied voltage), the cell size, and the size (e.g., diameter) of the nanostraw. The more charged a particular type of sample material is, the more quickly it will be released from within the cell, dependent on the size of the sample material and the applied electrical field. Further, the larger the diameter (e.g., opening size) of the nanostraw, the more sample material that may be released. Typically, stopping the application of voltage between the upper and lower electrodes and allowing the cell membrane to recover before more than 15% of the material within the cell is released may include stopping the application of a train of pluses of between 1 and 100 V having a pulse width of between about 10 microseconds and 50 milliseconds after a between 1 second and 300 seconds.

The sample may be captured (e.g., collected) in the sample collector in any appropriate manner. For example, the sample material may remain suspending in a fluid sample, and/or it may be immobilized on a substrate, including bound or captured to a substrate. For example, capturing the sample may comprise immobilizing the sample material onto a capture substrate.

In general, a plurality of nanostraws may be used, including a plurality within each of a plurality of sample regions, and/or plurality across multiple sample regions. For example, applying the voltage may comprise applying the voltage between an upper electrode and a lower electrode through the nanostraw and a plurality of additional nanostraws within a sample region. Further, capturing the sample may comprises capturing the sample material released into the nanostraw and the plurality of additional nanostraws in the sample collector. The nanostraws may be identical or different.

The steps described above (e.g., applying voltage, capturing sample material, etc.) may be repeated, for the same cell or cells, over time. For example, any of these methods may include repeating, after a minimum recover time, the steps of reapplying the voltage between the upper and lower electrode through the nanostraw, capturing sample material, and stopping the application of voltage, wherein the minimum recovery time is longer than one hour. Typically, the minimum recovery time may be longer than a few minutes (e.g., longer than 10 minutes, longer than 15 minutes, longer than 20 minutes, longer than 30 minutes, longer than 45 minutes, longer than 1 hour, longer than 1.5 hours, longer than 2 hours, longer than 3 hours, longer than 4 hours, longer than 5 hours, longer than 6 hours, longer than 12 hours, longer than 20 hours, etc.)

The method of claim 1, further comprising saving a first time sample from the captured sample material and repeating, for a plurality of additional repetitions after a minimum recovery time between each repetition, the steps of: reapplying the voltage between the upper and lower electrode through the nanostraw, capturing sample material, and stopping the application of voltage, wherein an additional time sample is saved from the captured sample material for each repetition.

A sample material may include a single type or species of material (e.g., a particular protein, mRNA, etc., which may be generally referred to herein as a biomarker) or the sample material may be a mixture of a variety of different sample materials. Any of these methods may include detecting the captured sample material captured in the sample collector. For example, any of these methods may include quantifying the captured sample material captured in the sample collector. Any of these methods may include identifying a plurality of different biomarkers from the captured sample material. For example, any of these methods may include quantifying a plurality of different biomarkers from the captured sample material.

A method of nondestructive sampling of intracellular sample material from within a cell at multiple time points, may include: applying a voltage of between 1 and 100 V between an upper electrode and a lower electrode through a nanostraw to open one or more pores in a portion of the cell membrane extending over an opening of the nanostraw; capturing a sample material released from within the cell and into the nanostraw in a sample collector beneath the nanostraw, wherein capturing comprises immobilizing the sample material onto a capture substrate; stopping the application of voltage between the upper and lower electrodes and allowing the cell membrane to recover before more than 15% of the sample material within the cell is released; and allowing the cell to recover for a minimum recovery time of at least 1 hour before reapplying the voltage and capturing additional sample material.

A method of nondestructive sampling of intracellular sample material from within a cell at multiple time points may include: applying a voltage between an upper electrode and a lower electrode through at least one nanostraw in each of a plurality of sample regions of a nanostraw substrate to open one or more pores through a cell membrane extending over an opening of each nanostraw; capturing sample material at each of the plurality of sample regions, wherein the sample material is released into the nanostraws to a plurality of sample collectors beneath the at least one nanostraw corresponding to each of the plurality of sample regions; stopping the application of voltage between the upper and lower electrodes; allowing the cell to recover for a minimum recovery time of at least 1 hour before reapplying the voltage and capturing additional sample material at each of the plurality of sample regions; and identifying a different biomarker from the captured sample material for each of the plurality of sample regions at different times.

Also described herein are apparatuses, including systems and devices, for nondestructively sampling intracellular material. For example, a system may include: a cell culture chamber having an upper region and a lower region; a nanostraw substrate positioned over the lower region, wherein the substrate comprises a plurality of sample regions; a plurality of nanostraws extending through the nanostraw substrate in each sample region, wherein each nanostraw has an outer diameter configured to support a cell without penetrating the cell's cell membrane; a plurality of sample material collectors, wherein each sample material collector corresponds to one sample region of the plurality of sample regions; a first electrode in the upper region; a second electrode in the lower region; and a controller coupled to the first electrode and the second electrode and configured to apply a pulsed voltage through the plurality of nanostraws of between about 1 V and 100V, a pulse width of between about 10 microseconds and 50 milliseconds for a duration of between 1 second and 300 seconds.

The nanostraw substrate may comprises a pattern of recessed sample regions. The pattern may be grid or any other pattern. The recessed sample regions may be recessed on one or both sides.

The nanostraw substrate comprises may be a removable capture substrate configured to be removably placed into the cell culture chamber. The nanostraw substrate may be keyed to fit within the cell culture chamber in a unique orientation (e.g., including a notch, cut-out, protrusion, or the like, and/or having a shape) that requires that the substrate be oriented in a specific configuration so that it can fit into and engage with the cell culture chamber.

The nanostraw substrate may be formed of any appropriate material; for example, the substrate may comprise a polycarbonate membrane.

The nanostraw substrate may comprise a blocking coating covering the surface of the nanostraw substrate between the sample regions, such as a blocking polymer coating. Thus, only the sampling regions may include nanostraws (or "open" nanostraws). In general, the thickness of samples regions of the nanostraw substrate is between 10 nm and 5 microns (e.g., less than 5 microns, less than 3 microns, less than 2 microns, less than 1 micron, etc.).

The lower region of the cell culture chamber may include a plurality of sample ports, wherein each sample material collector is associated with a unique sample port. For example, the lower region may correspond to the sample material collectors; in some variations the sample collectors may be separate from the bottom of the cell culture chamber and/or inserted into the cell culture chamber. If the sample material collectors are configured to collect material in liquid suspension, the material collector may include a fluid containing/storage region in addition to or instead of a sample port.

The nanostraws may be any appropriate size, typically for making contact with the cells without penetrating them. For example, the nanostraws may have an outer diameter between about 20 nm to about 1500 nm (e.g., between 100 nm and 1500 nm, between 150 nm and 1500 nm, greater than 150 nm, greater than 160 nm, greater than 170 nm, greater than 180 nm, greater than 190 nm, greater than 200 nm, etc.). For example, each nanostraw may have an outer diameter of greater than 100 nm.

The nanostraw may be made of any appropriate material, particularly non-sticky materials, such as alumina.

Each of the plurality of sample material collectors may comprises a sample material capture substrate configured to bind to the sample material (e.g. solid phase substrate, substrate to which a biding agent has been attached, membrane, including charged membrane, etc.). The sample material collectors may be removable.

The second electrode may be positioned between the nanostraw substrate and the plurality of sample material collectors. Alternatively, the plurality of sample material collectors may be positioned between the nanostraw substrate and the second electrode.

The plurality of sampling regions may each be configured to have a maximum diameter of between 5 µm and 200 µm (e.g. between 5 µm and 150 µm, between 5 µm and 100 µm, etc. e.g., less than 200 µm, less than 150 µm, less than 100 µm, less than 75 µm, less than 50 µm, less than 30 µm, less than 20 µm, less than 15 µm, less than 10 µm, etc.).

For example, a system for sampling intracellular material may include: a cell culture chamber having an upper region and a lower region; a nanostraw substrate positioned over the lower region, wherein the substrate comprises a pattern of recessed sample regions; a plurality of nanostraws extending through the nanostraw substrate in each sample region, wherein each nanostraw has an outer diameter configured to support a cell without penetrating the cell's cell membrane, wherein the outer diameter is between about 20 nm to about 1500 nm; a plurality of removable sample material collectors comprising a sample material capture substrate, wherein each sample material collector corresponds to one sample region of the plurality of sample regions; a first electrode in the upper region; a second electrode in the lower region; and a controller coupled to the first electrode and the second electrode and configured to apply a pulsed voltage through the plurality of nanostraws of between about 1 V and 100V, a pulse width of between about 10 microseconds and 50 milliseconds for a duration of between 1 second and 300 seconds.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 1a shows an example of a system using a polymer membrane with protruding nanostraws having an outer diameter of about 150 nm. This membrane connects the bottom of a chamber (e.g., a 5 mm glass cylinder) to an extraction buffer. For sampling, the NS well is removed from the incubator and placed on an electrode (e.g., an ITO electrode), as shown. A small quantity of the intracellular contents are sampled using an electrical pulse (or pulse train) to open holes in the cell membrane, allowing material to diffuse through the NS into the extraction buffer (pink). An aliquot of the buffer may then be aspirated with a standard pipette and analyzed conventionally, e.g., using fluorescence imaging, ELISA, qPCR, etc. FIG. 1b illustrates the active sampling using the apparatus shown in FIG. 1a. During sampling, intracellular species within the cell diffuse through the NS and into the extraction buffer below the membrane. In this example, the sampling region may be defined by a recessed region in the substrate (e.g., the NS membrane, shown here as a polycarbonate membrane). The size of the sampling region can be defined (e.g., lithographically) such that only the cells that grow in the active regions are sampled. FIGS. 1c and 1d show 45° tilted view scanning electron microscope (SEM) images of an approximately 150 nm diameter NSs and a 200×200 µm active sampling region using a system configured as shown in FIGS. 1a-1b. In this example, it was demonstrated that cells outside this window are relatively unaffected by the sampling process. FIGS. 1e and 1f show exemplary SEM images of cells cultured on (in FIG. 1e) a 50×50 µm active sampling region containing 42 cells, and (in FIG. 10a 15×15 µm sampling region used to isolate and sample from a single cell.

FIG. 2a shows fluorescent microscopy images of GFP (green channel, top) and RFP (red channel, bottom) of a culture of 38 cells on a 200×200 µm NS sampling region (dashed squares). Images were taken every 4 h just before the nanostraw extraction method (NEX) sampling method described herein was performed. RFP transfection was performed after the 8 h time point. FIG. 2b shows normalized cellular GFP contents from fluorescence microscopy compared to the NEX extracted GFP quantities. No statistically significant difference was observed between the relative extracted GFP level and relative intracellular GFP expression level from cells for each time point. Uncertainty bars reflect standard deviation of underlying signal (p>0.05 for both factors, two-way ANOVA). FIG. 2c shows normalized RFP fluorescence intensity compared to the extracted quantities. A small background signal was present before RFP transfection, yet the clear increase of extracted RFP correlated with the actual increase in RFP expression. Error bars denote s.d. (p<0.05 between time points, p>0.05 for extracted to fluorescence, double asterisk indicates P<0.01, triple asterisk indicates P<0.001, post-hoc Tukey test). FIG. 2d shows cell viability as a function of time (sampling points). Cultures showed >95% viability immediately after sampling, and >100% over time as the cells divided.

FIGS. 3a-3d show fluorescent microscopy images of a single RFP expressing cell on a 100×100 µm sampling region (dashed squares). RFP transfection was performed after the day 2 sample point. FIG. 3e shows calibrated RFP quantities in the cell from fluorescence compared to the extracted quantities. The extracted RFP amounts followed the increase in RFP expression within the cell.

In FIGS. 4a and 4b, fluorescent microscopy images of GFP of a culture of 26 cells on a 200×200 µm NS sampling region (white dashed squares) are shown. FIG. 4a shows GFP-expressing CHO cells before sampling, and FIG. 4b shows GFP-expressing CHO cells immediately after sampling. Locally diminished GFP intensities (dark spots, see, e.g., FIG. 10, below) were observed in the cells after sampling, likely corresponding to the locations where GFP was removed from the cells. Scale bar is 50 µm; the brightness has been increased to highlight the spots. FIG. 4c shows a diagram of a finite element model of sampling through the NS. In this example, the cell was treated as a 20×20 µm source that is 1 µm tall, connected to the extraction buffer by varying numbers of 14 µm long, 150 nm diameter NS. FIG. 4d illustrates an example of the percentage of the cell's initial GFP that diffuses into the extraction buffer as a function of time and number of NS, when modeled similar to FIG. 4c.

FIGS. 5a and 5b show longitudinal HSP27 extraction from the same hiPSC-CMs for 4 days. In FIG. 5a, the cardiomyocytes were stimulated by increasing the temperature to 44° C. for 30 min before sampling at day 2. An up-regulation of HSP27 was observed at day 3 (n=4, the asterisk indicates P<0.05, Tukey posthoc test, one-way ANOVA). The HSP27 level started to drop at day 4. In FIG. 5b, non-heat shocked hiPSC-CMs were longitudinally sampled for four days (n=4, P>0.05, one-way ANOVA test). FIG. 5c shows representative images of astrocytes derived from hiPSC in 3D cultures (hCS) and cultured in monolayer on NS. Astrocytes are labeled fluorescently with a lentiviral reporter (hGFAP: eGFP) and immunostained with an anti-GFP antibody. The morphology of astrocytes was maintained even after 20 days of culture and repeated sampling on the NS platform.

In FIG. 6a, mRNA expression level in NS-extraction (black) and from lysed cells (grey) in delta Ct (normalized to GAPDH). A higher delta Ct represents a lower mRNA expression, and the baseline delta Ct was set to 40 cycles to indicate no expression. Of the 48 genes (see, e.g., the table in FIG. 16, listing the size and name of the 48 analyzed genes) examined, seven genes were found to be statistically different from the lysis control (n=4 for living cell extraction, n=2 for cell lysis, single asterisk indicates P<0.05, double asterisk indicates P<0.01, t-test with 95% CI, pooled standard deviation. In FIG. 6b, mRNA sizes of matched and unmatched genes (single asterisk indicates P<0.05, t-test) shows a slight detection difference between larger and smaller genes. FIG. 6c shows a correlation of delta Ct of the 40 matched genes in living cell extraction with the mRNA expression level in cell lysis (R=0.89, p<0.0001, black dots: matched genes, gray dots: unmatched genes). In FIG. 6d, longitudinal mRNA expression level of ~15 hiPSC-CMs on 100×100 µm NS platform over 3 days is shown. Fifteen of eighteen genes showed consistent gene expression, showing the reliability of the sampling process. Error bars are the SD of technical duplicates. In FIG. 6e, microscopy image of ~15 hiPSC-CMs after day 3 sampling is shown. These cells were actively beating, yet could still be successfully sampled.

In FIG. 7b, a 10 nm film of aluminum oxide was coated on all the nanoporous surface of the polycarbonate membranes, in this example by atomic layer deposition using trimethyl aluminum and water as precursors. A pulse form of a-b-c was used for deposition, where a is the precursor exposure time (0.025 s), b is time for the precursor to retain in the ALD chamber (30 s), and c is the N$_2$ purge time (30 s). In FIG. 7c, a 5 µm thick positive photoresist film was spin-coated on the top surface of the ALD coated polycarbonate membrane, e.g., using a spinning speed of 3500 rpm for 60 s. The photoresist-coated membrane was baked at 95° C. for 2 min to evaporate resist solvent. In FIG. 7d, the photoresist-coated membrane was exposed to a square pattern of intense UV light for 5 s, and then was developed by immersing into the developer for 60 s. These two steps create a sampling region. In FIG. 7e, after photolithography, the aluminum oxide surface in the microwell was etched away, e.g., by a Plasma Quest reactive ion etcher (RIE) with a fast flow composition of 40 sccm BCl$_3$, 30 sccm Cl$_2$, and 5 sccm Ar at 300 watts at room temperature, leaving a polycarbonate surface inside the microwell. During the RIE, the unexposed photoresist served as a protection layer. Because the photoresist is much thicker than the alumina layer, the alumina layer inside the microwell can be fully remove without affecting the overall structure of microwells. In FIG. 7f, Oxygen RIE with 30 sccm O$_2$ at 300 watts was used to selectively etch the polymer until the desirable height of NS (e.g., between 10 nm to 10 µm, between 20 nm to 3 µm, etc., between 10 nm to 2 µm, between 10 nm to 1.5 µm, etc.) was obtained. The etching rate of alumina from oxygen RIE is slower compared to the etching rate of the polymer, thus the etching of alumina is negligible. The etching rate of both photoresist and polycarbonate are almost the same, so to make 1 µm tall nanostraws, 1 µm of photoresist will also be etched way. The photoresist was thick enough to allow fabrication of 3 µm nanostraws inside the microwell without completely removing the photoresist during etching. Thus, the photoresist can still act as blocking layer to cover the pores outside the microwell.

In FIGS. 8a-8f, isotachophoresis (ITP) was used to concentrate GFP and RFP at 10,000 times. ITP is a form of electrophoresis that focuses the target molecules in a focusing zone between two electrolytes with different ionic mobility (including g a leading and trailing electrolyte, LE and TE, respectively). After the complete formation of the ITP focusing zone, total FP mass can be quantified by measuring fluorescent intensity of the ITP zone images obtained with a fluorescence microscope and a CCD camera. In FIG. 8a, 3 to 10 µL of LE was injected at the LE reservoir and filled the entire channel. 1 to 5 µL of the sample and TE mixture was injected in the TE reservoir. In FIG. 8b, 1100V DC was applied between the two Pt electrodes placed at TE and LE reservoirs. In FIG. 8c, 2 min after the formation of ITP zone, the fluorescence intensity of the ITP zone was stabilized, indicating complete focusing of all GFP molecules in the microfluidic chamber. In FIG. 8d, time-resolved images showing the formation of an ITP zone (the white dash line indicates channel edges), at increasing distances in the microfluidic channel are indicated in the figure. In FIG. 8e, GFP intensity in the ITP zone over time (increasing distance) is shown. The fluorescent intensity value at each distance was extracted by averaging the intensity of ITP zone, as shown in FIG. 8f, showing GFP and RFP standard curves generated based on the measured intensity (n=3) from GFP and RFP standards diluted in the TE buffer.

FIG. 9 shows another example of longitudinal sampling. In FIG. 9, longitudinal sampling of GFP/RFP is illustrated from the same subpopulation of GFP expressing CHO cells. Fluorescent microscopy images of GFP (green channel, top) and RFP (red channel, bottom) of a culture of 48 cells on a 200×200 µm$^2$ NS sampling region (dashed squares) is shown. Images were obtained every 4 hours just before the NS sampling process was performed. RFP expression was observed starting at the 12 h time point, 4 hours after RFP transfection using lipofectamine.

FIG. 10 illustrates "dark spots" (regions where an intracellular component being sampled was diffused away by the method described herein). In FIG. 10, fluorescent microscopy images of GFP of a culture of 26 cells on a 200×200 µm NS sampling region (dashed squares) is shown. The dark spots as obtained by manual counting were labeled in red to indicate their location in cells.

FIGS. 11a and 11b illustrate a linear relationship between GFP/RFP concentration and intensity using the methods described herein. GFP and RFP solutions with concentration of 0.25, 0.13, 0.07, 0.04, and 0.02 pg/ml, were injected in a 10 µm wide and 12 µm deep glass microfluidic chamber. Microscopic fluorescence images of the GFP/RFP filled microfluidic chamber were obtained using (in FIG. 11a) 200 ms and (in FIG. 11b) 25 ms exposure time. The fluorescence intensity of the GFP/RFP solutions was measured (n=3, error bars show standard deviation).

FIGS. 12a and 12b show SEM images of cardiac cells on NS platform. In FIGS. 12a-12b, hiPSC-CMs are spread out on the NS substrate platform. As observed, the NS are not broken off by the beating of the cardiomyocytes, but instead, the nanostraws bend to accommodate the stress. Note the cells are dehydrated during the SEM preparation process, and thus the images are not indicative of cell morphology in culture. Instead, these images show the NS survive after culture with beating cardiomyocytes. Scale bar in FIG. 12a also applies to FIG. 12b.

In FIG. 13a, astrocytes are labeled with the hGFAP:: eGFP reporter and co-immunostained with an anti-GFAP antibody. In FIG. 13b, neurons are immunostained with an anti-MAP2 antibody, and are shown to not co-localize with hGFAP::eGFP+ cells. Scale bars: 50 μm.

In FIG. 14, intracellular localization of matched and unmatched mRNA is shown. Subcellular localization of the mRNA may affect the sampling efficiency. To examine this, mRNA was assumed to be localized to the same regions as the proteins that they code for. The protein localization was then compared in 12 subcellular locations of the specific unmatched gene to the matched gene. mRNAs that code for proteins found in the plasma membrane were statistically shown to be more often unmatched (P<0.05, t-test), which indicate that the specific mRNA sequences is more likely immobilized within the cytoplasm leading to low detection rate.

FIG. 16 is a table illustrating the sizes and names of the 48 analyzed genes (highlighted genes indicates unmatched genes).

In FIG. 17a, a capture substrate/ surface is placed below the nanostraw substrate (and may be swapped out/replaced at different times) to capture or collect the material being sampled from within the cell. In FIG. 17a, the bottom electrode is placed behind the capturing substrate/surface.

DETAILED DESCRIPTION

Figures 1A, 1B, 1C, 1D, 1E, 1F:
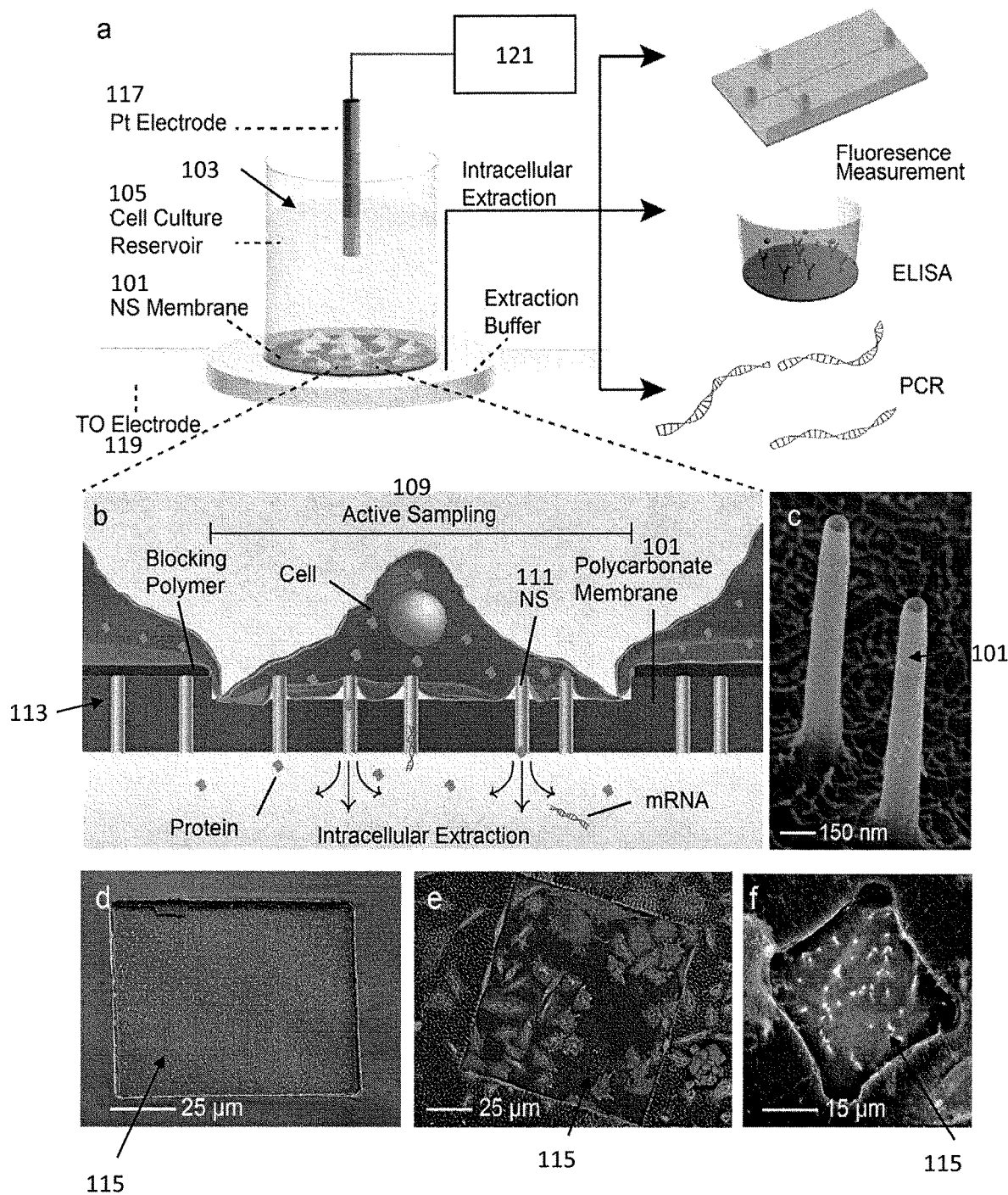
FIGS. 1a-1f illustrate one example of a nanostraw (NS) extraction sampling apparatus (e.g., system, device, etc.).

In general, described herein are methods and apparatuses for nondestructively sampling intracellular material. These methods and apparatuses may be based upon diffusively sampling material from inside the cell using a nanostraw (NS) embedded substrate. Typically, for example, cells of interest are cultured on a substrate (e.g., a polymer membrane) containing nanostraws, which may be localized to discrete regions (e.g., defined regions). The nanostraws are hollow and extend through the substrate and protrude from the surface of the substrate (see, e.g., FIG. 1a). For example, in FIG. 1a, the nanostraw substrate 101 is positioned a cell culture chamber 103 having an upper region (cell culture reservoir 105) and a lower region 107 holding an extraction buffer. The nanostraw substrate 101 is positioned over the lower region, and includes one or more active sample regions (see, e.g., FIG. 1b). The active sample regions 109 may be recessed. The substrate may have a pattern of such recessed sample regions. The pattern may be a grid pattern or any other arrangement of sample regions.

As shown in FIGS. 1a and 1b, a plurality of nanostraws 111 may extend through the nanostraw substrate 101 in each sample region 115. Each nanostraw may have an outer diameter configured to support a cell without penetrating the cell's cell membrane (e.g., the outer diameter may be between about 20 nm to about 1500 nm, or in particular, greater than 140 nm, e.g., 150 or greater, 200 or greater, etc.).

In general, an apparatus such as the system for nondestructively sampling intracellular material shown in FIG. 1a-1f may include a plurality of sample material collectors for collecting sample material released by the cell when the cell membrane is opened by applying a pulsed voltage through the nanostraw. The sample material collector 113 may collect liquid (e.g., extraction buffer into which the sample material is suspended) and/or it may include a bound sample material. For example, the sample collector 113 may include a sample material capture substrate. Any of these systems may include an array of sample material collectors, wherein each sample material collector corresponds to one sample region, and the paired sample regions and sample collector may be isolated from other sample regions and sample collectors.

In general, any of these systems for nondestructively sampling intracellular material may also include a first electrode in the upper region 117, and a second electrode in the lower region 119. A controller 121 may be coupled to the first electrode and the second electrode and configured to apply a pulsed voltage through the plurality of nanostraws. As mentioned, the pulsed voltage may be, for example, between about 1 V and 100V, having a pulse width of between about 10 microseconds and 50 milliseconds and may be applied for a duration of between 1 second and 300 seconds. The controller may be specifically adapted to apply the driving voltage within this range of values, and may be adjustable. For example, the user may adjust the applied peak voltage, pulse duration, and/or duration that the pulsed voltage is applied. The controller may also limit (e.g., prevent) the apparatus from applying additional voltage until after some minimum recovery time, which may be pre-set (e.g., to 4 hours or more) or may be user-selected to a value that is, e.g., between 1 hour and 48 hours, during which time, further applied voltage may not be applied.

When the cells are cultured on the substrate, the cells may grow normally over the entire substrate (e.g., polymer membrane), such that cells within the sampling region interact with surrounding cells, avoiding cell isolation. Intracellular samples may be collected by applying an electrical voltage through the nanostraws (NSs), locally opening small holes in the cell membrane near the NS tip. The applied energy may be configured such that, during the subsequent interval (e.g., typically between 2 to 5 min) when these pores are open, ~5-10% (e.g., less than 15%) of the proteins, mRNA and small molecules may diffuse and/or migrate based on charge from out of the cells, through the NS, and into an extraction solution below the culture well (see, e.g., FIG. 1b). Any appropriate extraction buffer may be used as long as it has a reasonably osmolality-matched to the cell; typically, e.g., 1× phosphate-buffered saline solution (PBS) may be used. After this interval (e.g., the 2-5 min interval), the sample material released from within the cell and into the nanostraw that is collected in a sample collector beneath the nanostraw (e.g., in the extraction buffer and/or any solid phase support) may be removed from the sample collector and analyzed conventionally, including fluorescence, mRNA detection, or ELISA assays. The cell culture well may then returned to an incubator until a new sample is required. In some variations the sample collector(s) under the nanostraws may be removed and/or replaced.

The methods described herein (which may be referred to herein as the NEX process) may be used to extract, evaluate and analyze one or more preferably many different intracellular components (e.g., protein and/or mRNA contents) both statically and longitudinally. These methods and apparatuses have been found to be nondestructive and may provide quantitatively useful information about intracellular contents for mRNA sequences and proteins. Notably, the methods and apparatuses described herein had >95% cell viability that enabled multiple, real-time sampling over extended time periods, and was well tolerated over 20 days by human astrocytes derived from hiPSCs. Equally important is the sampling process extracted species throughout the cell, providing a comprehensive view of expression rather than a single site extraction location. The system may be used for some, but not all, larger nucleic acid molecules (>15,000 nt) even despite slower diffusion and limited cytosolic accessibility. NEX sampling was successful even for single cells, although the small quantities of material extracted at this level restricted applicable analytical methods. Overall, the NEX process appears to be a straightforward method to non-destructively follow temporal dynamics of cellular protein and mRNA contents over time.

Figure 10:
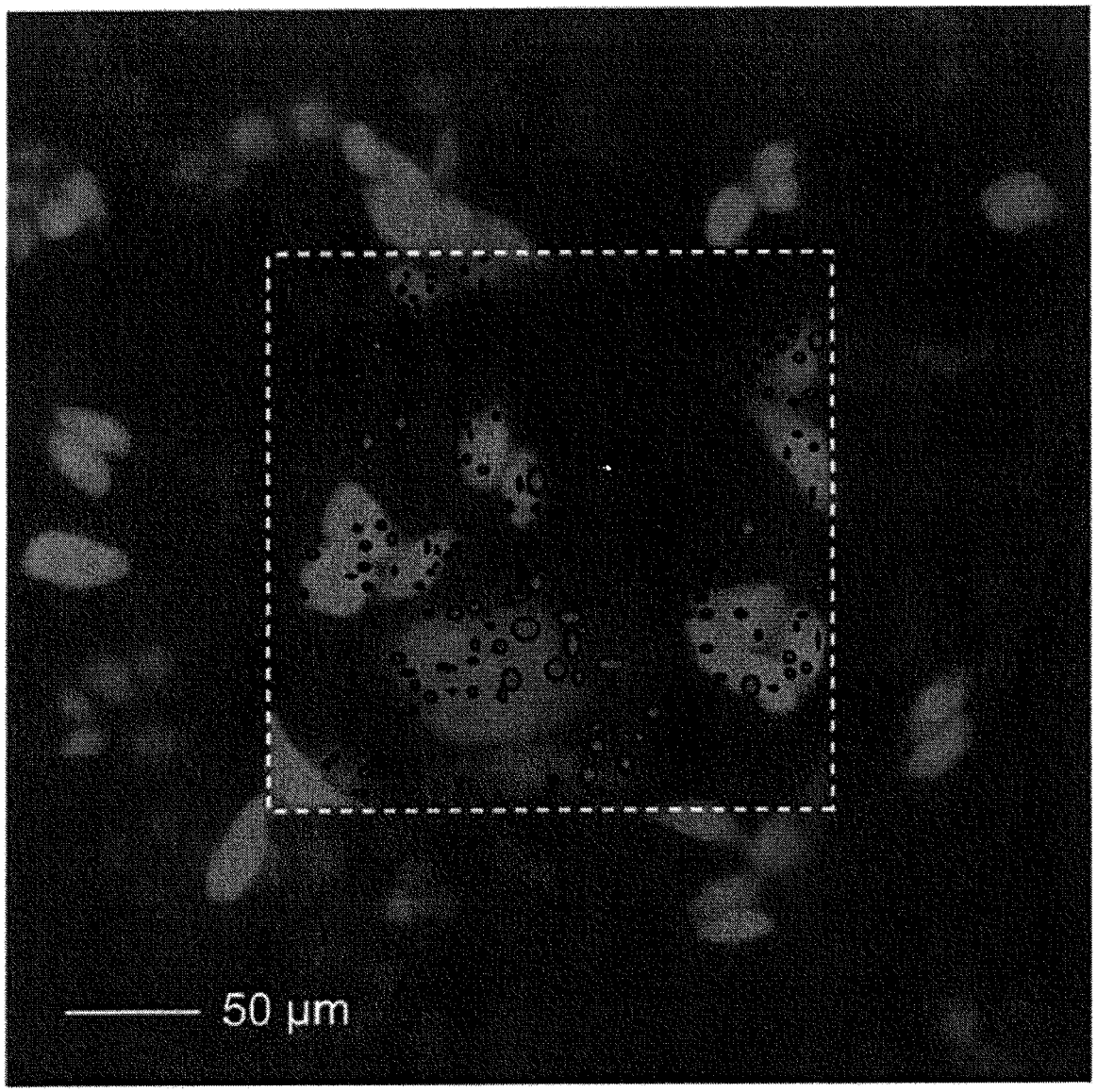

The NEX platform described herein may be based on a substrate including a (e.g., polycarbonate membrane) including a plurality of nanostraws. In FIG. 1c, for example, the NSs have an approximately 150 nm outer diameter, forming an inorganic NS extending through the polymer and protruding 1-3 microns above the surface. In FIGS. 1a and 1b, this NS membrane is mounted on the bottom of a 2-5 mm diameter glass cylinder 101 that fits into a 48- or 96-well plate for cell culture. Fabrication of the NS membranes is illustrated and described in FIG. 7a-7f; in this example, producing flat polycarbonate membranes with NS extending from the surface (see, e.g., FIG. 1c), where height is readily controllable. Specific cell-sampling regions may be defined, e.g., by blocking the remainder of NS membrane with blocking coating such as a photolithography-patterned polymer (See, e.g., FIGS. 7a-7f). During cell culture, only the cells that grow in the selected regions with exposed NS will be sampled, leaving cells on the blocked area unaffected (FIGS. 1d and 1e). The size of the sampling window can be adjusted from <1 micron on a side to millimeters, allowing scalable sampling from a single cell to a hundred thousand, while maintaining cell-to-cell connectivity and communication (e.g., FIGS. 1e and 10).

Cells grown on the NS described herein have been found to demonstrate normal cell behavior and mRNA expression, as shown in FIG. 1c. Typically, for many cell types, 100 nm or smaller diameter NS spontaneously penetrate the cell membrane, allowing delivery of small molecules into cells. Larger NS (e.g., 110 nm or larger, 120 nm or larger, 130 nm or larger, 140 nm or larger, e.g., such as 150 nm and larger) are instead engulfed by the cell membrane without causing membrane rupture. However, access to the cytoplasm can still be gained by applying short electric pulses (e.g., pulses of between about 10-35 V) to temporarily open small pores on the cell membrane at the NS-cell interface. The energy applied may be configured so that two to five minutes after the pulses, the cell membrane recovers and the cells evolve unperturbed. In order to prevent systemic cytosolic leakage, in some examples (e.g., using between about 110 and 1000 nm diameter, e.g., about 150 nm diameter NS) the use the electrical pulsing maybe controlled a 'valve' to gate sampling. The methods and apparatuses may therefore titrate when cells release contents through the NS, while maintaining their membrane integrity throughout the remaining culture period.

Figures 2A, 2B, 2C, 2D:
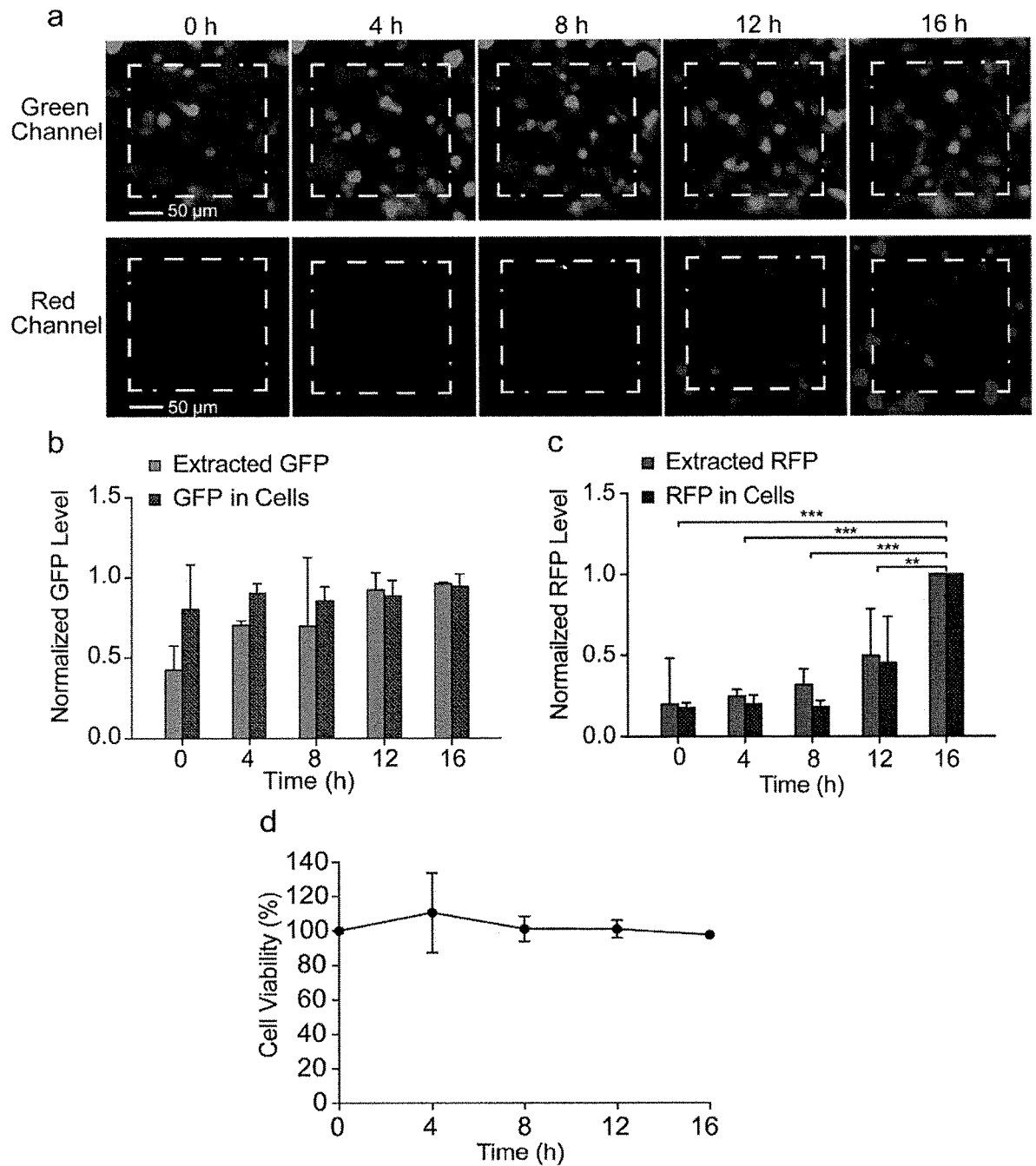
FIGS. 2a-2d illustrate an example of the methods and apparatuses described herein used to provide longitudinal sampling of GFP/RFP from the same subpopulation of CHO cells.
Figures 3A, 3B, 3C, 3D, 3E:
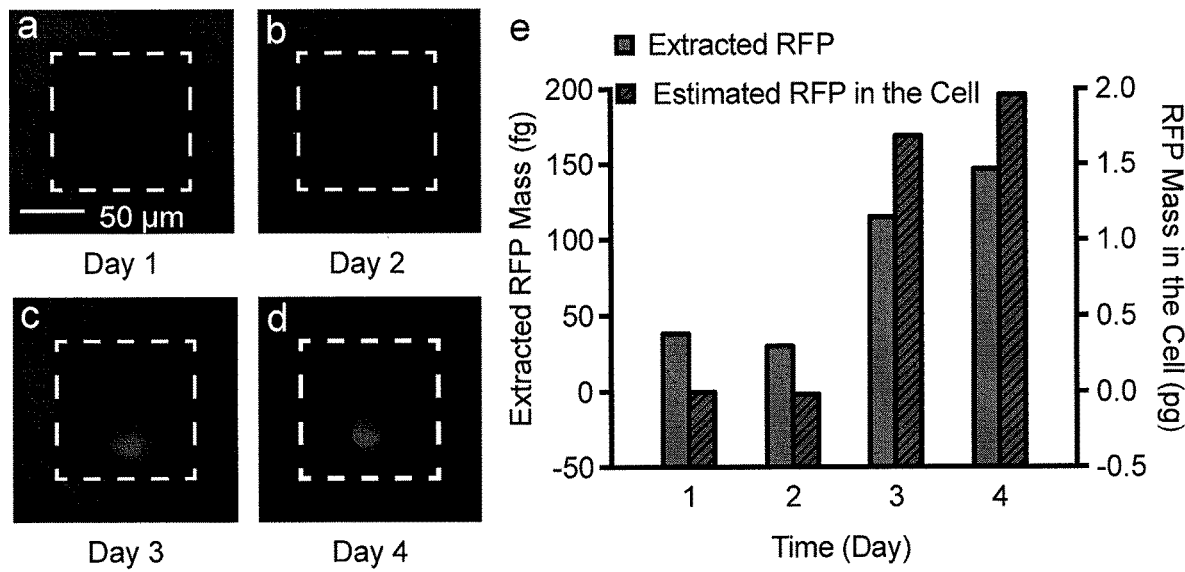
FIGS. 3a-3e show longitudinal sampling of RFP from a single CHO cell.
Figure 9:
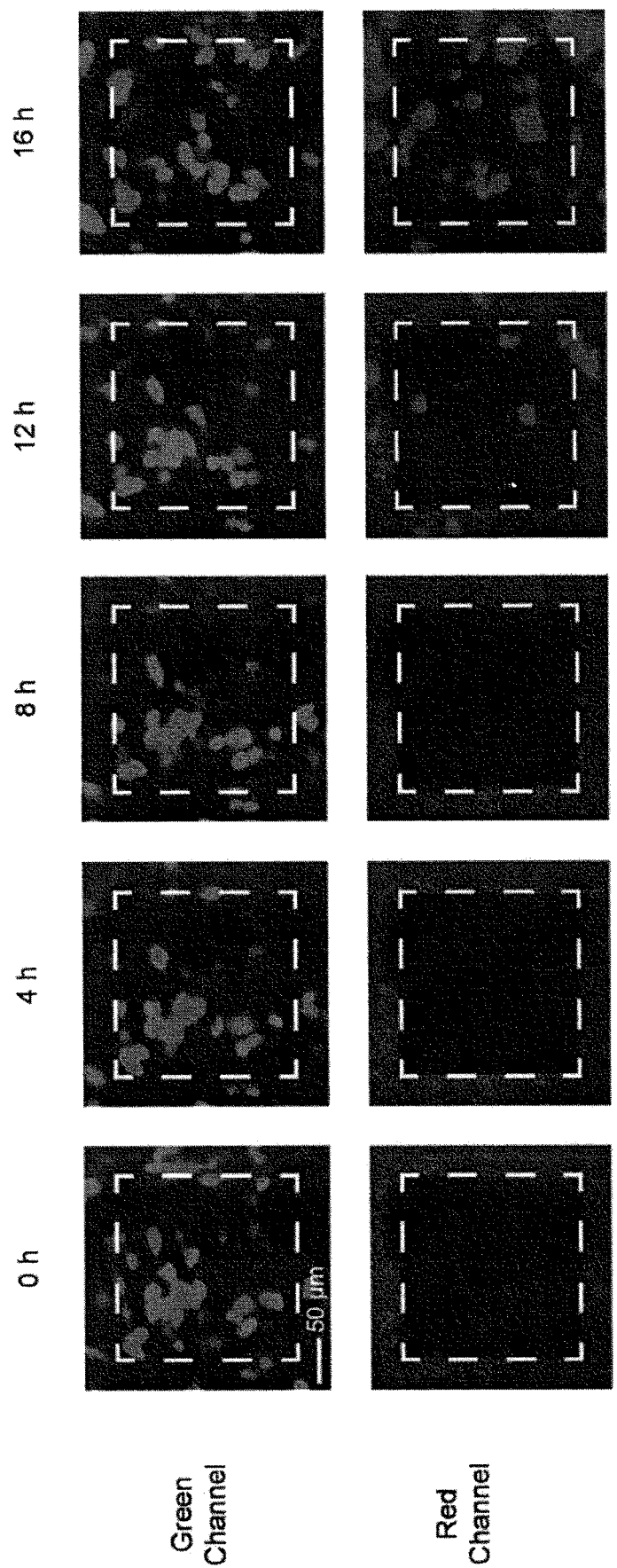

These methods and apparatuses may therefore allow real-time, longitudinal sampling from cell subpopulations and single cells, as described in FIGS. 2a-2d. In this example, the NEX sampling process was evaluated for quantitative analysis of intracellular protein concentrations within the same set of cells over time. A level of GFP fluorescence in NS-derived samples was extracted and measured and compared these values with the GFP fluorescence of the sampled cells. GFP-expressing CHO cells were cultured on the NS membrane with a 200×200 μm active area that mounted on a 2 mm glass cylinder. Cells were sampled every 4 h for 16 h total (e.g., at five time points, see FIG. 2a, columns). Dynamic changes in expression were examined by lipofectamine-transfecting with a plasmid containing RFP at the 8 h time point, for which expression became observable at 12 and 16 h. At each sampling point, the NS well was removed from the incubator, washed with PBS to remove possible contaminants, and the GFP and RFP intensity of the cells on the NS window was measured with fluorescent microscopy (FIG. 2a). In this example, a series of short electrical pulses were applied for 20 s, opening small holes in the cell membrane at the NS tips, and the cellar proteins were allowed to diffuse through the NS and into the extraction buffer for 10 min. The NS well was then returned to the incubator, and the amount of GFP/RFP in the extraction buffer was analyzed with fluorescence using isotachophoresis (ITP) to selectively concentrate the proteins (see, e.g., FIG. 8a-8f for a description of this technique). Normal cell morphology was observed throughout the experiment, and cell viability was >95% per sampling on average (FIG. 2d) indicating the cells were healthy during and after the sampling process. Experiments on sister cultures (e.g., FIG. 9) did not show qualitative differences.

FIG. 2b shows the quantitative comparison of the cells' GFP fluorescence by microscopy, and the NS-extracted GFP/RFP intensities from the 38 cells in the active NS region. The measurements were normalized to the highest value in each run in order to account for the different number of cells present, and averaged to provide standard deviations. The mean GFP expression level in the sampled cells did not show a significant change, as expected for a stably expressing protein. The NEX extracted GFP accurately followed this trend. The relative NEX-measured GFP levels did not show significant statistical difference (Two-Way ANOVA) with the GFP expression level in cells ($p>0.05$ for both time and extracted to fluorescence comparison) at any of the five time points. The extracted GFP signal was however significantly lower at the first time point, which was systematically observed for all NEX experiments, suggesting the initial extraction is less efficient. Thus, while not rising to the level of statistical deviation, the initial data point should usually be discarded, though we show all samples in this work. See, e.g., FIG. 2a-2d.

The NEX methods described herein (e.g., methods for nondestructive sampling of intracellular sample material from within a cell) can also follow temporal dynamics, namely the change in RFP as the cells begin to express RFP fluorescent proteins after transfection (see, e.g., FIG. 2c). Extracted RFP levels were equal to the background fluorescence for the first 3 time points, then increased quickly at 3 and 4 days, in agreement with microscopy images ($p<0.001$, Two-way ANOVA). No significant difference between NEX extracted amounts to the fluorescence imaging was observed ($p>0.05$, Two-way ANOVA). The sampling process could thus also measure dynamic changes in cell expression over time.

Encouraged by the results on this subpopulation of 38 cells, the active NS area was reduced to 100×100 μm to sample a single cell (See, e.g., FIG. 3a-3e). In this example, the cell was sampled once a day for a 4-day period and RFP contents were analyzed using ITP (see, FIG. 3a-3d) and compared to fluorescence microscopy images. After sampling at day 2, the cells were transfected with an RFP plasmid using lipofectamine. One cell in the NS active area fluoresced on day 3, and intensified on day 4. The absolute quantity of RFP may be determined, e.g., using a calibration curve (See FIGS. 11A-11B) for both the microscopy and NEX measurements, allowing direct quantitative comparison. FIG. 3a-3e shows the calibrated mass of cellular and extracted RFP from a single cell. The extracted RFP expression trend and the actual cell concentration were in good quantitative agreement relative to their initial baselines. The total RFP mass inside the cell was 1.7 pg and 2.0 pg at day 3 and 4, respectively, compared to 120 fg and 150 fg for the extracted RFP at those sampling points. This corresponds to an extraction yield of 7% and 8% of the total cellular RFP at the third and fourth sampling points, respectively.

The NEX process is configured so that only extracts a fraction of the total contents of the cell (e.g., 15% or less), hence the reason it is non-destructive, and therefore a relative calibration is necessary to infer absolute intracellular concentration. However, the extraction quantities over repeated sampling in FIGS. 2a-2d and 3a-3e show that each sampling event is highly consistent, and although extraction percentages vary somewhat from cell to cell the longitudinal extraction quantities are precise. For example, in two different single cell measurements one cell may give a 5% extraction efficiency and another 10%, yet each sampling event consistently yields the same percentage from each cell (e.g., FIG. 3e). Thus the method is capable of not only detecting the presence of an analyte, but reliably quantifying the cytosolic quantities over time.

Figures 4A, 4B, 4C, 4D:
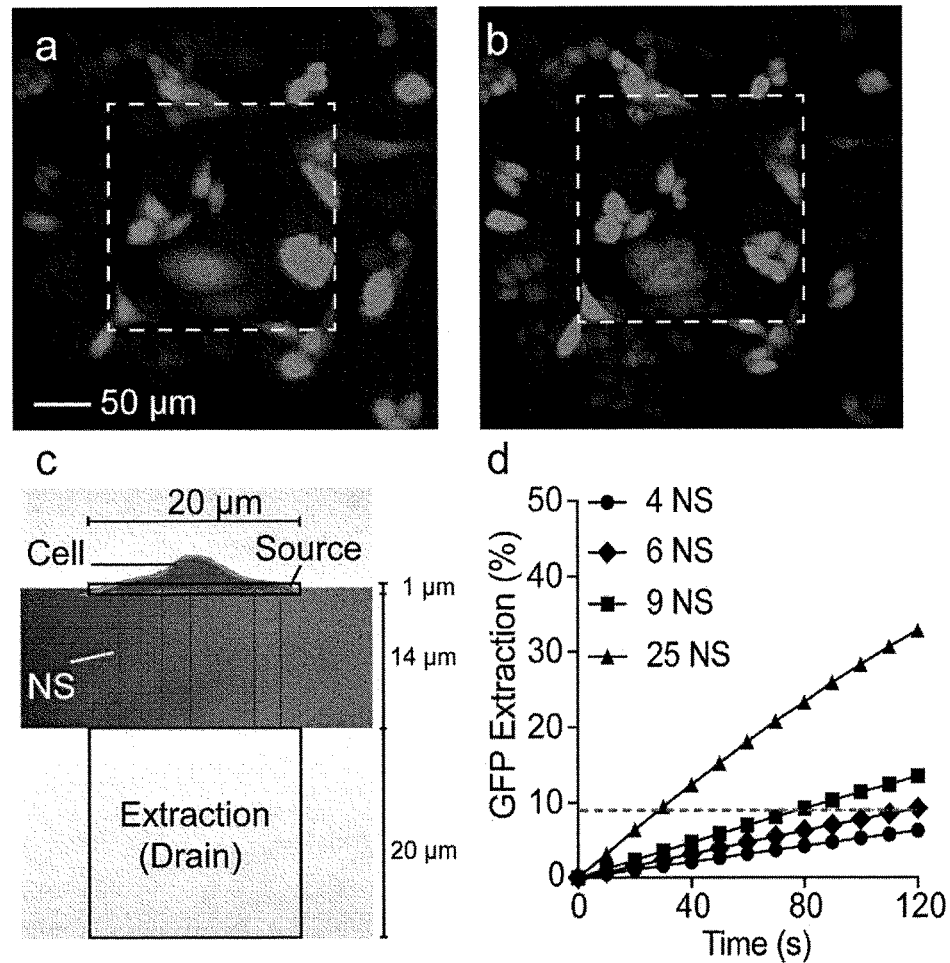
FIGS. 4a-4d illustrate the sampling spatial distribution using the methods and apparatuses described herein.

The apparatuses and methods described herein may also allow for spatial distribution and efficiency of sampling. The NEX process may be configured to reflect the contents of the entire cell, or samples only a single site. The spatial distribution of NS extraction from the decrease of GFP intensity within GFP-expressing CHO cells during sampling was assessed. CHO cells were cultured overnight on a patterned membrane with 200×200 μm region of ~40,000 exposed NS (see, e.g., FIG. 4a). During the 2 min sampling period, GFP diffuses out from the cells and through the NS, leaving a lower fluorescence intensity region (dark spots) in the cell where the membrane was opened (FIG. 4b). The location and number of 'open' NS can therefore be visualized by the dark spots in cells. Twenty-four out of twenty-six CHO cells showed spots during sampling demonstrating that most cells within the sampling region are penetrated and sampled through the NS. The multiple penetrating NS (dark spots) were observed to be distributed throughout the cell bodies, with little difference between the soma and peripheral regions. NEX thus appears to sample from all regions of the cytoplasm, providing a comprehensive view of the intracellular contents. See, e.g., FIGS. 4a-4d.

The total GFP extracted from the cells during sampling could be measured from the fluorescence intensity difference before and after sampling. The average GFP in a cell before and after sampling in this example was approximately 0.50 (+0.44) pg and 0.47 (+0.38) pg, calculated from a calibrated volumetric GFP intensity curve (See FIGS. 11a-11b). The GFP extracted from these 24 cells was 680 fg from the change in fluorescence intensity, or 6% of the initial cell concentration. This fraction is also similar to the single cell extraction percentages in FIGS. 3a-3d (7% and 8%). Since we know the amount of material the cells lost, we also calculated the collection efficiency. The calibrated amount of GFP measured in the extraction buffer during this same experiment was 230 fg, or ~30% of the total amount lost from the cell. This is reasonable collection efficiency, indicating the material loss during extraction and handling is not limiting. Together, these results show that most of the cells within the sampling region were extracted from, that multiple NS penetrate the cell at one time, that molecules were sampled from multiple regions of a cell, and that cell contents are extracted and analyzed with a reasonable collection efficiency.

In theory, the amount of material extracted may be a function of the cellular concentration, the diffusivity of the species, and the NS geometry. The extraction was simulated as a purely diffusive transport process using a finite-element model (COMSOL Multiphysics, Palo Alto Calif.) of a cellular volume (20 μm diameter; 1 μm tall), connected to the 1×PBS extraction buffer through a set of 14 μm long, 150 nm diameter NS (FIG. 4c). The expected percentage of the total GFP extracted from the cell as a function of time for a GFP diffusivity of 87 μm/s is shown in FIG. 4d, and agrees with our experimental observations. For 6 penetrating NS, close to the observed number of spots per cell (FIG. 4b), ~9% of the total GFP diffuses into the extraction buffer over the 2 min extraction interval, which corresponds well with the 7% and 8% GFP measured from the single cell experiments. See, e.g., FIGS. 5a-5c.

The apparatuses and systems described herein may also permit longitudinal sampling of proteins from hiPSC-derived cardiomyocytes and astrocytes. For example this apparatus, including the apparatus and methods described in FIGS. 1a-4d illustrate the operation of the methods described herein.

Figures 5A, 5B, 5C:
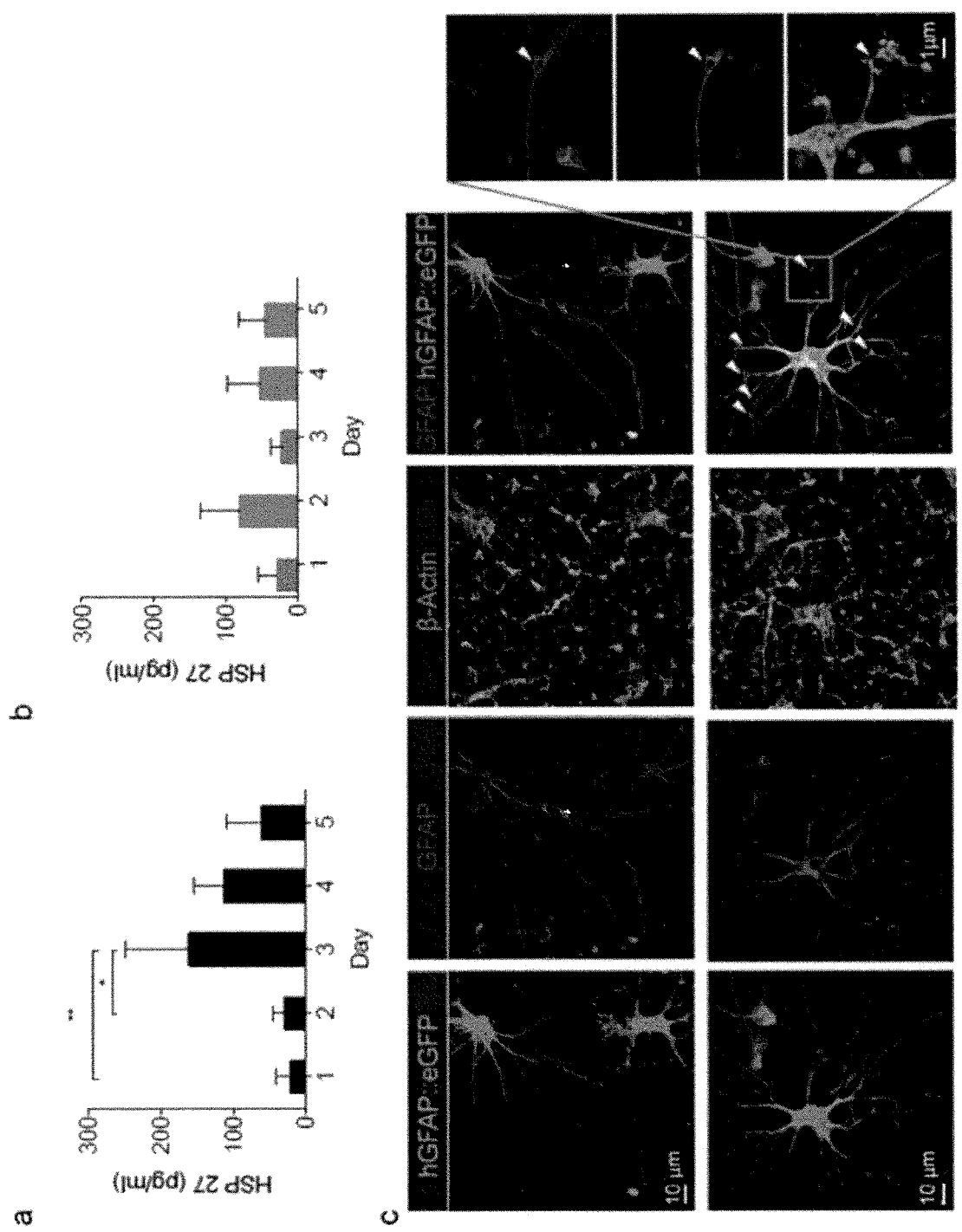
FIGS. 5a-5c illustrate one example of longitudinal sampling from human induced-pluripotent stem cells (hiPSC) derived cardiomyocytes and astrocytes.

The NEX methods can be used to sample contents not just from cell lines but also for cell types derived in vitro from human induced pluripotent stem cells (hiPSC), which is essential in future applications related to cell differentiation and disease modeling. We assessed longitudinal extraction and off-platform analyses of non-fluorescent heat shock protein 27 (HSP27) from hiPSC-derived cardiomyocytes (hiPSC-CMs), measured with ELISA (FIG. 5a-5c). Heat shock protein is upregulated when exposed to external stressors, and is thus suitable for studying transient processes, as descried herein.

Figures 13A, 13B:
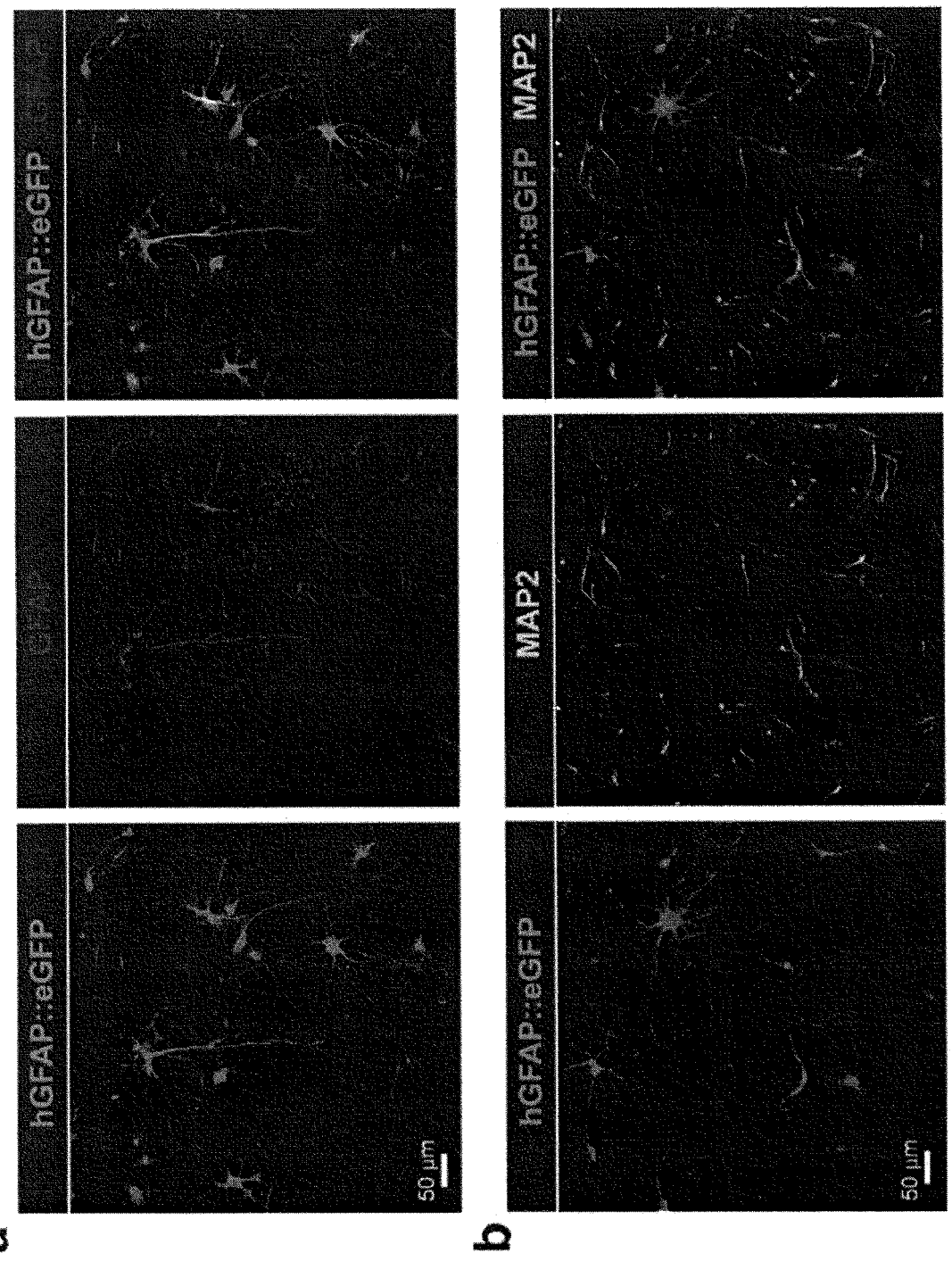
FIGS. 13a-13b illustrate the use of the methods and apparatuses described herein with iPSC-derived astrocytes and neurons generated in 3D hCS and cultured in monolayer on NS.

In one example, we increased the hiPSC-CM plating on our NS platform to 100,000 (±25,000) cells due to the detection limit of HSP27 ELISA (10.9 µg/ml, Affymetrix, San Diego Calif.), which is not sensitive enough to detect the intracellular extraction from small cell populations. See, e.g., FIGS. 12A-12B. After 7 days in culture on the NS, the hiPSC-CMs began beating. Even under stress from the continuous beating, the NS did not break nor were pulled from the cells, allowing sampling even from this actively moving tissue (FIGS. 13A-13B). Intracellular extractions were obtained every 24 h for 5 days. At day 2, the cells were stressed by exposure to a heat shock (44 C for 30 min), which is expected to upregulate the synthesis of HSP27. A sister culture not exposed to the heat shock perturbation were sampled at the same time points as a negative control.

The NS platform followed the temporal expression and upregulation of HSP 27 in human CMs. Starting with a relatively low concentration at day 1, there was a small but not statistically significant HSP27 level increase 2 h after heat shock perturbation at day 2, suggesting delayed expression of HSP27. At day 3, the HSP27 increased about 5 times higher than at day 1 and 2 (n=4, P<0.05, one-way ANOVA), and then decreased at day 4 and 5. In contrast, the HSP27 level of the control was relatively constant all four days (n=4, P>0.05, one-way ANOVA test). The first extraction point showed lower extraction levels in both sets of data, similar to what was observed for the GFP sampling experiment. The small upregulation of the HSP27 in the control samples indicates minimal stress response due to sampling, and Calcein AM labeling confirmed >90% cell viability for both sample and negative control. These results demonstrate the feasibility to use the NS to extract and measure non-fluorescent proteins from beating hiPSC-CMs.

In order to assess the influence of the long-term culture on the NS platform and repeated sampling process on neural cell types, we examined the viability of astrocytes derived from hiPSC in 3D cortical spheroids (hCSs). Approximately 50,000 astrocytes and neurons derived in 132-day old hCS were plated on the NS platform (FIG. 6c), and electrically porated using the same protocol for the cardiomyocytes once per day for 20 days. Astrocytes were fluorescently labeled with a cell-specific reporter (hGFAP::eGFP) as previously described. Cell morphology was followed every day during the sampling period, and despite their high overall reactivity to various stimuli and cell injuries, human astrocytes cultured on the NS tolerated the platform and the daily sampling well, with insignificant morphological changes between day 1 and day 20.

The methods and apparatuses described herein were also used to detect and/or measure mRNA expression levels in human iPSC derived cardiomyocytes, for example the particular mRNA transcriptomics. Measuring the apparent these mRNA expression levels in human iPSC derived cardiomyocytes may prove to be a powerful method to detect gene expression, cell phenotype, and cell to cell heterogeneity. With the advent of efficient reverse transcription and single-cell sequencing, multiple mRNA sequences can be simultaneously detected and with higher sensitivity than proteins. To test whether the mRNA extracted from primary hiPSC-CMs are statistically related to the actual concentrations inside the cell, we first performed a NEX extraction of mRNA for 2 min and compared it to the mRNA expression for a lysed sister cell preparation. The NEX extract was pipetted from below the well and amplified with RT-PCR using a random primer and sequenced with a single-cell BioMark system. The results were compared to the positive control (n=2) obtained by lysing a sister culture of hiPSC-CMs, and a negative control without the electroporation step (n=4). Both of these controls were amplified and analyzed in the same manner as the mRNA samples. Among the 48 genes, 25 were cardiac-related genes, including an inward-rectifier potassium ion channel (KCNJ2) and several integral membrane proteins (e.g., PLN, SCN5A), 13 were stem cell differentiation related genes and 10 were housekeeping genes.

Figures 6A, 6B, 6C, 6D, 6E:
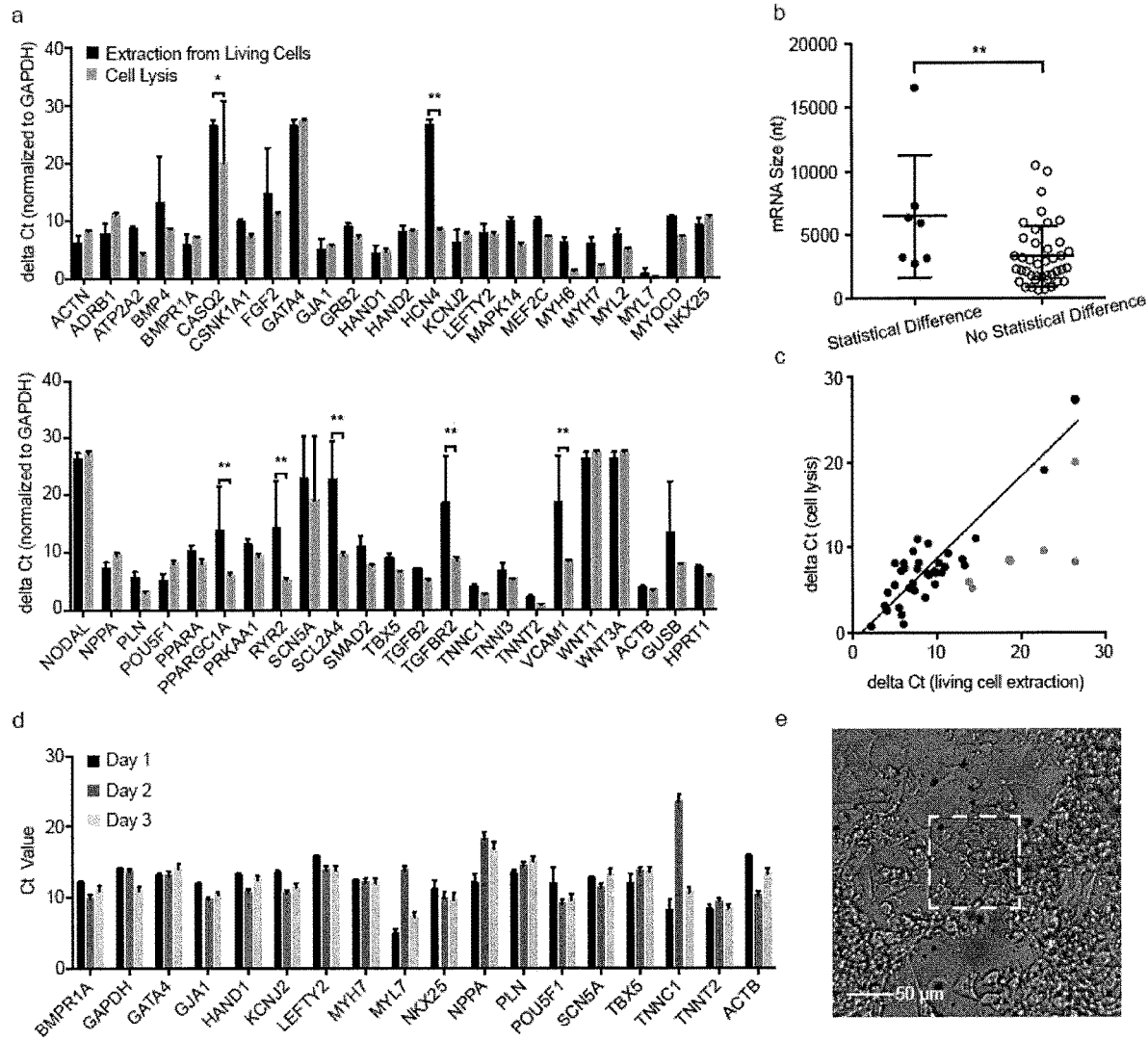
FIGS. 6a-6e illustrate mRNA expression level in extraction from hiPSC-CMs using the methods described herein.
Figures 7A, 7B, 7C, 7D, 7E, 7F:
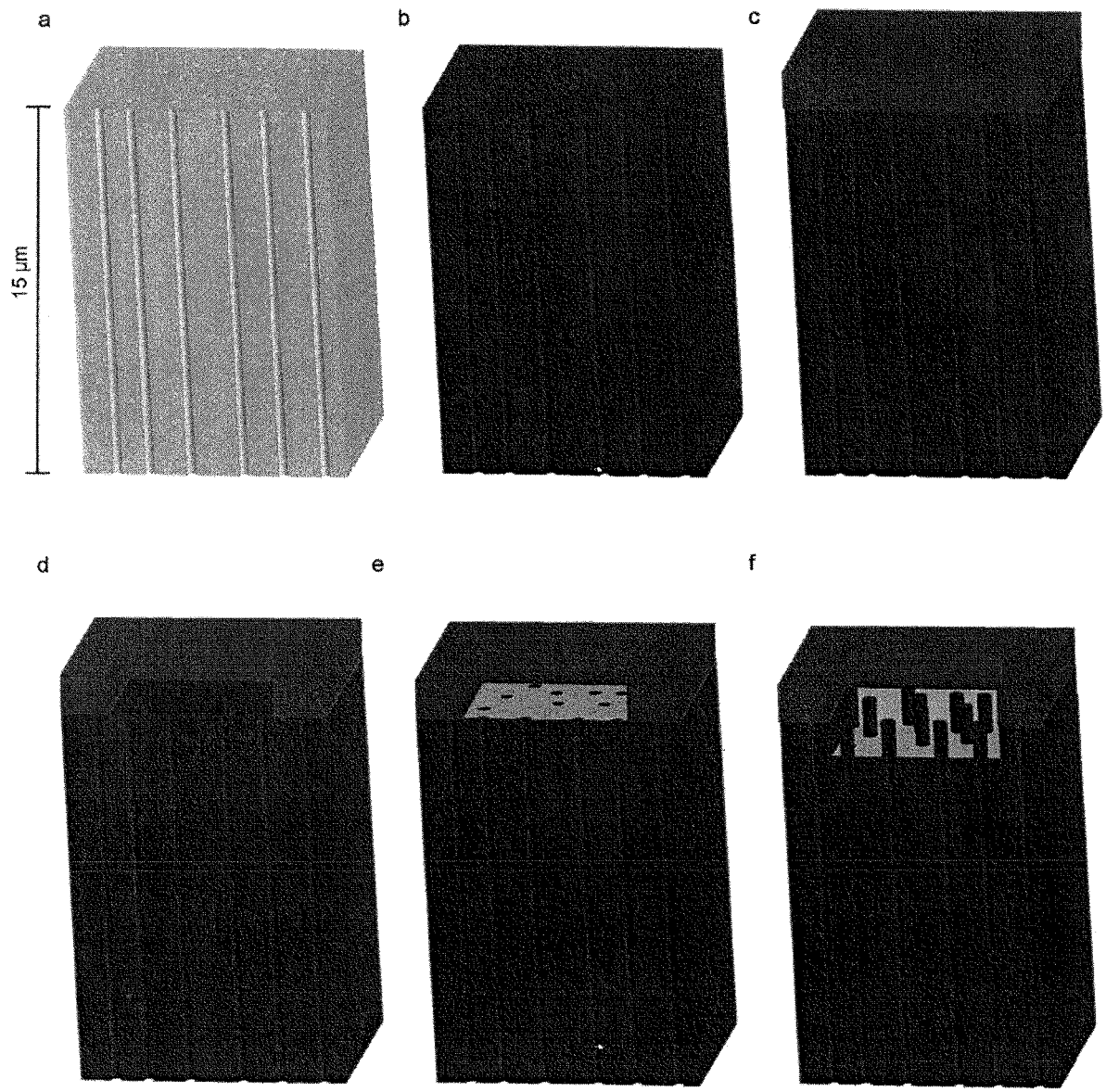
FIGS. 7a-7f illustrate one example of a technique for forming patterned nanostraws (NSs) as part of a substrate for any of the apparatuses described herein. In this example, a patterned NS sampling platform was fabricated starting with (in FIG. 7a) a track-etched polycarbonate membrane having a 150 nm pore diameter and pore density of approximately $1 \times 10^8$ pores/cm$^2$ (any appropriate pore diameter, including, e.g., between $1 \times 10^4$-$1 \times 10^9$ pores/cm$^2$, may be used).
Figures 8A, 8B, 8C, 8D, 8E, 8F:
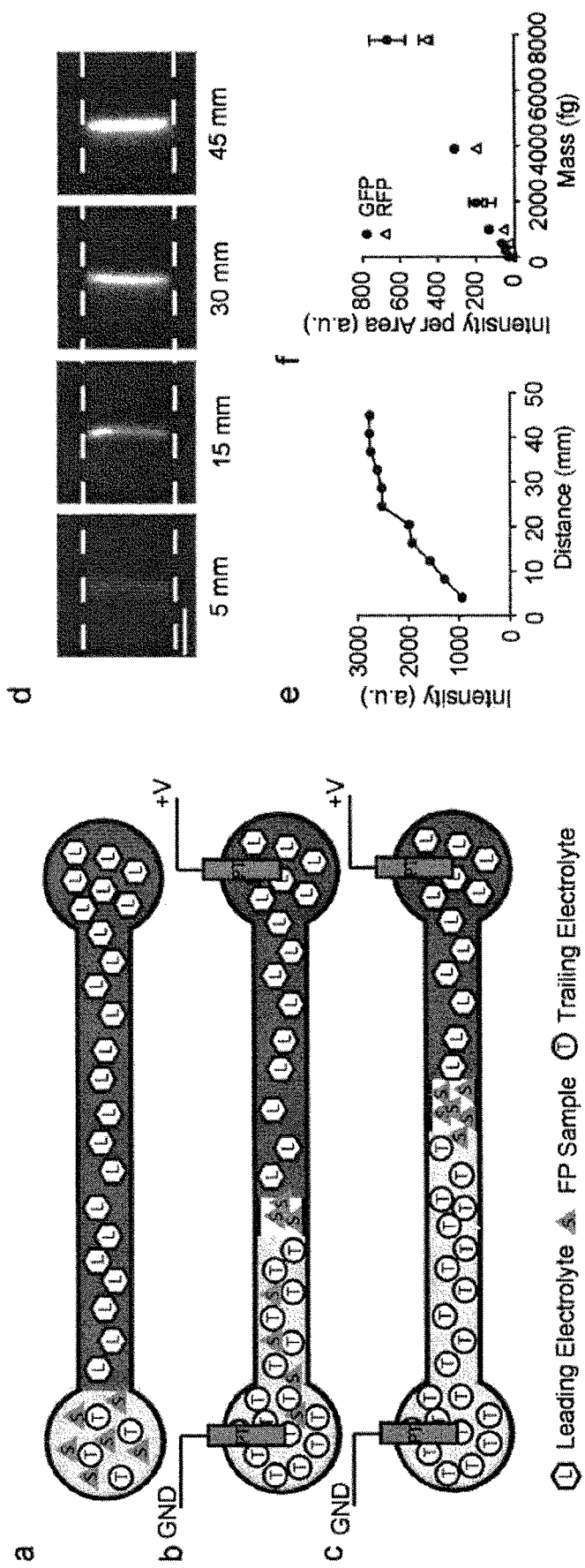
FIGS. 8a-8f illustrate one example of a method (and calibration technique) that may be used in conjunction with the methods and apparatuses described herein.
Figure 14:
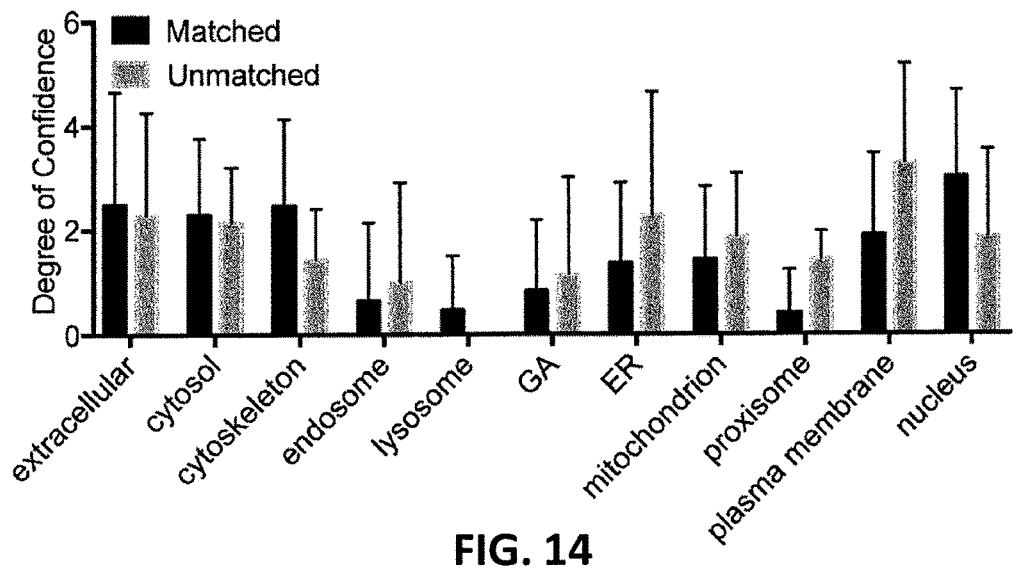
FIG. 14 graphically illustrates the co-localization of mRNA using the methods as described herein.

The mRNA from the NEX extracts were in good quantitative agreement with the lysis control samples. All genes with non-zero quantities from lysis were also detected in the NEX extraction, equal to 44 gene detections for each sample. No false positives were observed, as the 4 mRNA that were not detected in the positive controls were also not detected in the cell extraction. The delta Ct of each gene (excluding the statistically unmatched genes) in the extraction was strongly correlated with the positive control (FIG. 6c, R=0.89, P<0.0001). Notably even large genes such as SMAD2 (10,428 nt) were successfully sampled (see the table in FIG. 16). After sampling, the hiPSC-CMs showed healthy morphology and the green fluorescence from the calcein AM stain indicated >95% cell viability. Negative controls with electric field, but no NS, showed no detectable signal, as shown in FIG. 14.

Statistical t-test analyses of the 44 detected mRNA sequences found that only seven genes were significantly different than the control (P<0.05, t-test) shown as light gray dots in FIG. 4c. The lower detection efficiency of the seven unsuccessful genes could be due to several factors, including lower diffusion rates due to size or binding to structures within the cell. We did not include a statistical multiple testing correction intentionally because such a procedure, while maintaining the overall type I error rate, increases the chance of type II errors (the chance that differentially extracted genes are not discovered). FIG. 6b shows a slight statistical difference between the sizes of the unmatched and matched mRNA (P<0.01, t-test), suggesting larger size molecules are more difficult to extract during the 2-5 min extraction period, though the result was heavily influenced by RYR2 at 16,562 nt. Subcellular localization of the mRNA may also affect the sampling efficiency, as mRNAs that code for proteins found in the plasma membrane were statistically more often unmatched (FIG. 14, P<0.05, t-test).

The methods (e.g., NEX sampling) described herein may be repeated on the same set of actively behaving primary cells to provide longitudinal mRNA measurements. FIGS. 6d-6e show mRNA expression levels of 18 different genes from ~15 hiPSC-CMs measured once per day for three days. Note these cells were active and beating at the time they were sampled. The presence of additional cell monolayers makes exact cell counting difficult, however on average 15-20 cells were observed on the 100×100 µm sampling region. The measured expression levels were remarkably consistent, demonstrating the precision of the sampling and analysis process. Of the 18 genes, 15 were highly consistent over three days, implying the variations in MYL7, TNNC1, and ACTB are likely significant and may reflect fluctuations in gene expression. More work is necessary to definitively establish the biological origin of these fluctuations, yet it is clear the NEX process has the capacity to measure the change or lack of change in mRNA expression over time from the same set of cells.

Currently the sensitivity of mRNA sequencing systems are not able to measure NEX extracts from single cells, instead requiring ~15 to 20 cells. This agrees well with the ~7% extraction efficiency, corresponding to ~1.1 to 1.4 cellular equivalents per sample. With the increasing sensitivity of single cell mRNA assays this limitation may soon be overcome, enabling repeated mRNA measurements from a single cell over an extended time period.

Any of the NS substrates descried herein may be patterned and fabricated. The NS membrane may be based on 15 μm (±15%) thick track-etched polycarbonate membranes (GVS, Sanford) with 1×10 pores/cm, often used for water filtration and cell culture. A 10 nm thick $Al_2O_3$ layer is deposited on the membrane using atomic layer deposition (ALD) at 110 C, including the insides of the track-etched pores which will become the NS walls. The NS are formed by reactive ion etching the $Al_2O_3$ with $BCl_3$ and C12 in Argon (300 W, 40 sccm $BCl_3$, 30 sccm C12, 5 mTorr, 5 min) from the top surface to reveal the polymer, followed by oxygen plasma etching to remove the polymer and expose the inorganic NS. To fabricate the photolithographically defined sampling regions, a 5 μm thick positive photoresist film (e.g., MEGAPOSIT SPR2203 i-Line photoresist, Dow, Austin) was spin coated on the surface of the ALD coated polycarbonate membrane using a spinning speed of 3500 rpm for 60 s. Next, the photoresist-coated membrane was baked at 95 C for 2 min to evaporate resist solvent, and then the photoresist-coated membrane was exposed to a square pattern of intense UV light for 5 s. After exposure, the membrane was developed by immersing into the MF-26A developer (Shipley, Marlborough) for 60 s. The aluminum oxide surface in the sampling region was etched away by RIB, leaving a polycarbonate surface inside the sampling region. Finally, the polymer was etched away by oxygen RIE in order to form the NS.

In any of the methods and apparatuses described herein, prior to extracting material from the cells through the nanostraws as described, the cells may be cleaned to remove excreted material and dead cell fragments. For example the cells may be rinsed in a buffer (e.g., phosphate buffered saline, PBS). In general, cells may be kept in one or more different buffers (e.g., PBS or TE buffer), rather than using cell media, and rinsed to remove media prior to sampling. Surprisingly, the use of cell media resulted in an apparent contamination of the sampled portion (e.g., the captured sample material). This may be due to proteins and sugars contained in cell media which could show up as contaminants in the sampled contents. After sampling, cells may again be bathed in media. Thus, any of the apparatuses described herein may be configured to rinse and/or replace the solution (e.g., switching between cell media and media-free buffers) between sampling. Thus the cell culture chamber of the apparatus may include ports for adding/removing the material surrounding the cells growing on the substrate; the apparatus may include tubing and/or pumps to add and/or remove (and switch between the media and buffer) automatically prior to and/or after sampling.

In any of the methods and apparatuses described herein, as already mentioned, the substrate containing the nanostraws may include a plurality of different sample regions. For sampling, these sample regions may be defined (e.g., lithographically defined) sample region, and may be marked, or visible. Sample regions may be recessed relative to the rest of the substrate onto which the cells are grown. Open nanostraws for sampling may be present only in the sample regions.

Also, in any of these methods and apparatuses, the polarity of the electric field may be reversed (e.g., compared to delivery of material into the cells) such that negatively charged species will be mobilized out from the cells.

Any of the apparatuses and methods of using them descried herein may include a sample preparation for scanning electron microscopy: for example, a NS membrane may be prepared for SEM imaging by sputter coating with about 10 nm of Au/Pd. Biological samples were prepared by fixing in 2% Glutaraldehyde with 4% Paraformaldehyde (PFA) in 0.1M Na Cacodylate Buffer (pH 7.3) for at least 4 h, next, stain with 1% $OsO_4$ for 10 min, and followed by dehydration in a series of 30, 50, 70, 90, and 100% ethanol with 10 min of incubation at room temperature for each solution. The dehydrated sample was dried by critical point drying in 100% EtOH with liquid $CO_2$, and then sputter coating with about 10 nm of Au/Pd for SEM. Samples were imaged in a FEI Sirion SEM.

Figure 15:
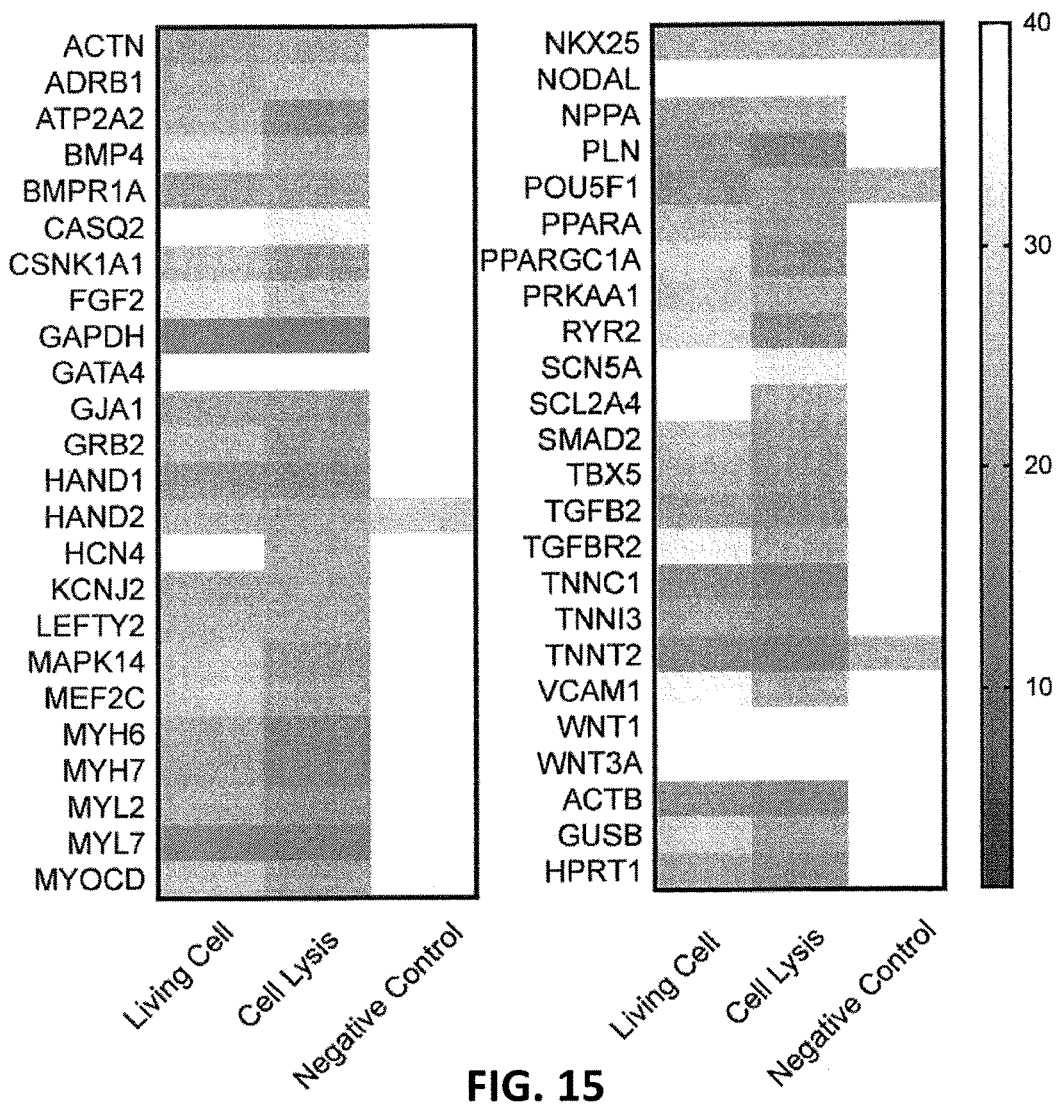
FIG. 15 graphically illustrates a comparison between detected levels for 48 different genes as sampled by the methods described herein (e.g., nanostraw extraction/diffusion "living cells," control lysed cells and negative control (without electrical pulsing)). The heat map shown in FIG. 15 illustrates that the cytoplasmic level of 48 genes from living cells matched well with control (cell lysis) results. Very low or no gene signal was detected in the negative control collected after washing (without electroporation using the nanostraw extraction), indicating the washing step is sufficient to remove the background contamination.

To perform the sampling process described, the cells of interest were first cultured on the NS membrane within a 2-5 mm glass cylinder with appropriate cell media on top (FIG. 1b). This culture tube remained within a 96 (or 48)-well plate in an incubator until a sample was desired. The sampling process was performed in five steps: First, the cells were washed with 1× phosphate-buffered saline (PBS) three times and the cell culture media was changed to PBS to eliminate possible contaminants. See, e.g., FIG. 15. Second, the NS cylinder was placed on top of a droplet of 1-15 μl extraction buffer consisting of PBS, or TE buffer for the ITP assay (explained in later section) on an indium tin oxide (ITO) electrode (FIG. 1a). A platinum (Pt) wire was immersed into the cell culture buffer which will act as the counter electrode. Third, 10-45 V (between anode and cathode) square electric pulses were applied for 20-60 s (200 μs pulse duration, 20 Hz repetition rate) between the two electrodes (across the NS membrane). The pulses temporarily opened pores in the cell membrane, allowing freely diffusing intracellular proteins and mRNA to diffuse through the NS to the extraction buffer on the underside of the NS membrane. We have observed an increased flux of molecules when the polarity of the electric field is the opposite of the charge of the analytes. When extracting negatively charged molecules (e.g. mRNA), the ITO electrode was kept at positive potential, whereas it was kept negative when extracting positively charged molecules. Fourth, after the electroporation, the sampling device was kept on the extraction buffer for another 0.5-5 mM to allow diffusion of additional cytosolic content. Because the extraction process depended mainly on molecular diffusion, the total amount of extracted molecules was expected to depend on both diffusivity and concentration. Therefore, for extraction of larger molecules, longer diffusion time was expected due to their lower mobility. Finally, the extracted molecules were collected beneath the NS membrane for further analysis by pipetting up the extraction buffer.

The second electrode may be an ITP electrode. ITP was conducted in a 50 μm wide, 20 μm deep cross-channel design glass microfluidic chip. The leading electrolyte (LE) and trailing electrolyte (TE) buffers were 200 mM of tris and 100 mM of HCl, and 25 mM of tris with 150 mM of glycine, respectively. 1% Polyvinylpyrrolidone (PVP) was added to both LE and TE to suppress electro-osmotic flow (EOF). All reagents were obtained from Sigma Aldrich, Mo., USA. The TE buffer was also used as the extraction buffer in cell sampling. To pre-concentrate GFP, first, the microfluidic channel and LE reservoir were filled with 3 to 10 μL of LE, and then 1 to 5 μL mixture of TE and GFP sample solution was injected in the TE reservoir. Next, anode and cathode were placed in the LE and TE reservoir respectively. An electric field with 1100 V (Keithley, Beaverton) was applied between the electrodes. The GFP ITP focusing zone formed and electromigrated towards anode right after applying the electric field. The GFP intensity was stabilized 2 min after the ITP starts. See, e.g., FIGS. 8a-8f.

To obtain a detectable protein signal, in some variations we increased the cell population on our NS platform to 50,000 (±25,000) cells due to the detection limit of HSP 27 ELISA (10.9 µg/ml, Affymetrix, Santa Clara), which is not sensitive enough to detect the intracellular extraction from small cell populations. Intracellular extractions were obtained every 24 hours for 5 days. Cells were washed in PBS before each sampling in order to remove loosely adsorbed proteins. At day 2, the cells were stressed by exposing them to a 30 min heat shock at 44 C, which is expected to upregulate the synthesis of HSP 27. The day 2 extraction was collected 2 h after the heat shock. Cells not exposed to the heat shock perturbation were also sampled as a negative control.

RNA Extraction from hiPSC-CMs may be performed using the methods and apparatuses described herein. For example, mRNAs may be extracted using the NS followed by amplification and analysis using RT-PCR and qPCR. In order to average out stochastic fluctuations associated with small numbers of cells, we chose to culture 100,000 (+50,000) cells in a NS well. The cells were rinsed with PBS buffer to remove extraneous or excreted material, then sampling was performed for 2.0 min as described previously. Since mRNA rapidly degrades in the presence of RNase, carrier RNA (Sigma Aldrich, St. Louis) and RNase inhibitor (Thermo Fisher Scientific, Waltham) was added to the extraction buffer to make a mixture with 1 µg/ml and 1 U/pt respectively before sampling. The mRNAs in the extraction buffer were reverse transcribed to cDNAs with Oligo(dT)20 (Thermo Fisher Scientific, Waltham). Next, the cDNAs were pre-amplified for 15 cycles and purified using DNA Clean & Concentrator™5 (Zymo Research). The pre-amplified cDNAs were then amplified with the 48 gene primers and analyzed by qPCR in an integrated fluidic circuits Fluidigm chip following standard protocols (Fluidigm, Palo Alto).

To pre-amplify the extracted mRNA, 0.5 µl DEPC-treated water, 0.5 µl Oligo(dT) and 0.5 µl dNTP reagent was mixed with 5 µl mRNA extraction. The mRNA solution was mixed and briefly centrifuged, and then heated at 65° C. for 5 min and incubated on ice for at least 1 min. 2 µl 5×SSIV buffer, 0.5 µl DTT, 0.5 µl RNase inhibitor and 0.5 µl SuperScript IV RTase were added into the annealed RNA solution. The combined reaction mixture was incubated at 50° C. for 20 min, then the reaction was inactivated by incubating the mixture at 80° C. for 10 minutes. 10 µl Pooled assay mix, 20 µl TaqMan PreAmp Master Mix was added to the combined reaction mixture. Sixth, the mixture was preamplified at the following conditions: HOLD for approximately 15-20 CYCLEs: Temp of about 95° C. (10 min), cycled for 15-20 cycles at 95° C. (15 secs) for 60° C. (4 min). Finally, the preamplified cDNA was purified using DNA Clean & Concentrator™-5, eluted in 6 µl DNA Elution Buffer. The preamplifed cDNA was detected by using Fluidigm Dynamic Array IFC for Gene Expression.

The methods and apparatuses described herein may also be configured to culture and perform GFP extraction and Immunocytochemistry of hCS-derived astrocytes. Human cortical spheroids (hCS) were derived from iPSC as previously described. The generation of neurons of deep- and superficial-cortical layers is followed by astrogenesis in hCS, and after ~10 weeks in vitro cortical neurons are accompanied by a network of non-reactive astrocytes. For sampling experiments, hCS at day 132 in vitro were enzymatically dissociated and plated on NS at a density of 500,000-750,000 cells per device. The day after plating, plated astrocytes were labeled with a viral reporter (hGFAP:: eGFP). For GFP sampling, cells were maintained on the NS for up to 20 days with daily media changes. Short electrical pluses (45 V, 200 us pulse width, and 20 s duration) were applied to cells every day. For immunocytochemistry, the cells on NS were fixed with 4% PFA for 10 minutes and immunostained with an anti-GFAP antibody to label astrocytes, an anti-MAP2 antibody to label neurons (MAP2) and anti-Actin antibody to label filaments.

Measuring dynamic intracellular processes and capturing cellular heterogeneity, especially at the single cell level, has become an area of active investigation in molecular and cellular biology. Despite rapid technological advancement in the sampling modalities and sensitivity, these methods are still limited by the need to lyse the cell for sample extraction. The methods and apparatuses described herein provide a sampling platform based on NS for longitudinal, non-destructive extraction and quantification of proteins and mRNAs from living cells. The procedure itself is quite straight-forward, locally porating a small area of the cellular membrane near the NS and allowing cellular contents to diffuse into an underlying extraction buffer. The process requires simple equipment and a common voltage supply, and should be feasible in most laboratories.

Extraction through passive diffusion as described herein has not been found to significantly bias the results to only a few of the possible species. Proteins and mRNA were sampled consistently over a wide range of sizes, and a similar percentages of the cellular content as smaller species has been found. While there was a slight preference for smaller mRNA (see, e.g., FIG. 6b), this was largely due to the influence of RYR2; without that data point there would have been no statistical difference. The fact that a large fraction ($41/48$) of the mRNA sequences were successfully analyzed suggests that a sufficient number of genes can be monitored to make meaningful biological assessments.

Another important aspect is the NEX process was non-perturbative, evidenced by >95% cell viability after each sampling event. Minimal morphological changes were observed even after sampling every day for 20 days from human astrocytes, which are known to react promptly to perturbations. Cell viability is a critical metric for longitudinal studies. For example, 80% cell viability per sample can take an average of 3 samples before cell death, while 95% viability gives an average of 14 samples. This will be especially important for longitudinal measurements of single cells, where cell apoptosis terminates the experiment.

There are several other key features that make NEX suitable for longitudinal studies of cell biology. First, the extracted molecules are spatially separated from the cell culture, allowing for simple collection using a pipette or microfluidic device. This ensures that future analytical technology improvements can be combined with the NEX process as the sampling platform. Second, the patterned NS sampling region allows scalable numbers of cells to be analyzed, while maintaining the normal cell-to-cell connectivity and communication important for cell development and differentiation. Third, the NS platform was compatible with all cell types tested, including cell lines (CHO) and hiPSC-derived cells (cardiomyocytes or neural cells derived in 3D cultures).

This sampling technique may therefore be useful for studying dynamic cellular activity or transformations, for example tracking signaling pathways during differentiation of pluripotent stem cell in vitro and capturing cellular heterogeneity. The throughput could be increased by integrating microfluidics to sample from a number of independent cellular wells at once, similar to 96-chamber single cell analysis designs. Such systems could impact on the understanding of the cellular mechanisms behind cell development, differentiation, and disease pathology from bulk populations down to single cells.

Figure 17A:
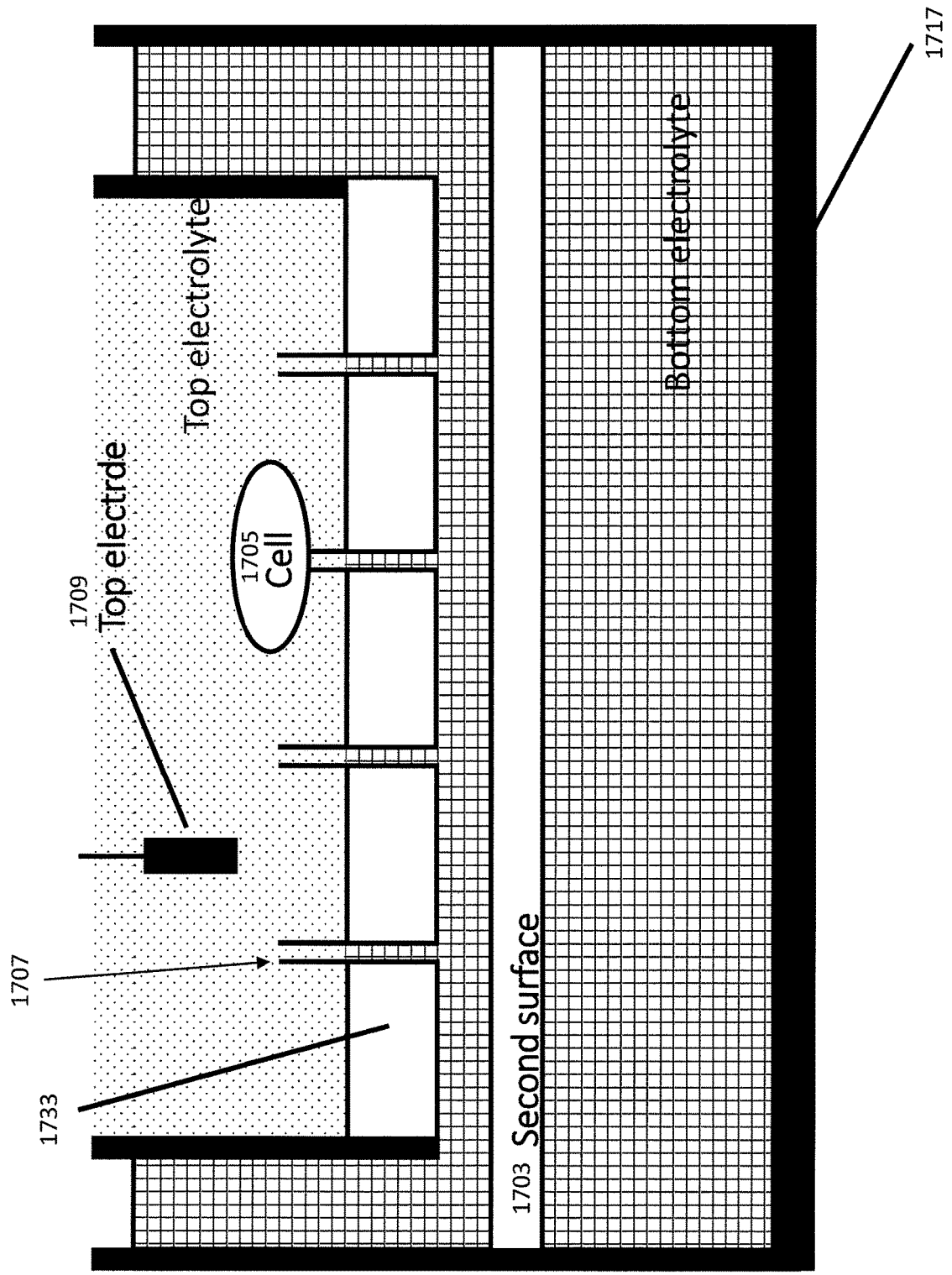
FIG. 17a shows a first example of an apparatus configured for spatial sampling (and/or sampling over time) of intracellular material using the nanostraw sample extraction methods described herein.
Figure 17B:
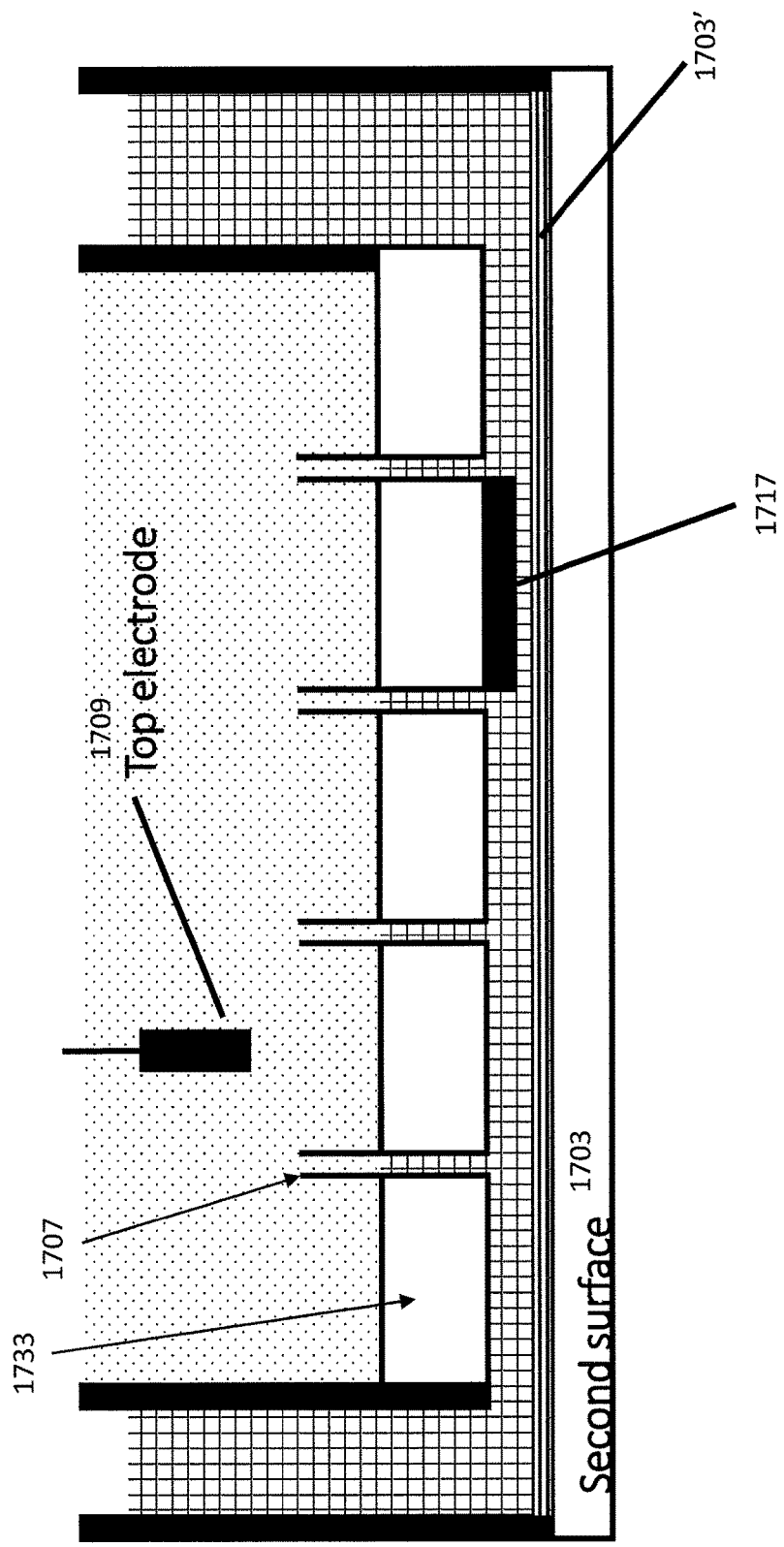
FIG. 17b shows another example of an apparatus configured for spatial sampling (and/or sampling over time) of intracellular material. In this example, the capture substrate/ surface may be at the bottom of the apparatus (and removal swapped out) and the bottom electrode may be above the capture surface (e.g., adjacent to the base of the nanostraw(s).

For example, FIGS. 17a and 17b illustrate examples of apparatuses, similar to that shown in FIG. 1a-1b that are configured to spatially resolved sampling. For example, in some of the apparatuses described herein (e.g., FIG. 17a), a second surface 1703 (e.g., a removable sample material collectors) may be positioned immediately underneath the nanostraw membrane 1733, so that the molecules that are extracted from the cells 1705 through the nanostraws 1707 can be physically or chemically bound to the second sample material collector(s) when the sample material exits the nanostraws 1707 on the bottom of the nanostraw membrane 1733.

Placing the second surface 1703 (e.g., removable sample material collector(s)) in close proximity to the nanostraw membrane 1733 (e.g., within tens of micrometers) may allow the extracted molecules to bind before they have time to diffuse away laterally, so that the two dimensional spatial resolution of the cells on the nanostraws may be preserved. This configuration may therefore allow the creation of a map of extracted molecules on the removable sample material collector(s) that corresponds to the positions of the cells on the nanostraw membrane, and we will be able to tell what cell each of the extracted molecules came from.

As mentioned above, in any of these variations, the removable sample material collectors may be removed or replaced with each repetition of the sampling procedure, providing a time course from the sampled cells. For example, the nanostraw membrane 1073 may be placed on the second removable sample material collectors (e.g., surface) to capture extracted cellular content (sample material), and then the nanostraw membrane, on which the same cells are still attached and relatively undisturbed, may be moved to another removable sample material collector(s) to collect sample material at a different time point. By repeating this with new removable sample material collectors, samples of the content of cells over time with preserved spatial resolution down to or below single cell resolution may be achieved. At any point during this time course, a simulation or perturbation of the cells (e.g., heating, adding a material, etc.) may be added to stimulate or otherwise test the cell.

This method and apparatus may therefore be able to follow the molecular content of individual cells over time in a massively parallel way (e.g., up to thousands of cells at the time).

As mentioned above, any appropriate removable sample material collector may be used. For example, the removable sample material collector can be a permeable membrane that the molecules to capture can go into or bind onto, or it can be a solid support for example glass, metal, or plastic. The captured molecules (sample material) can, for example, be physically adsorbed, e.g., electrostatically bound in an oppositely charged polymer membrane. For example, mRNA is negative and can be electrostatically bound in a positively charged polymer membrane. The removable sample material collector may be a solid support, and may have capturing agents on it. Depending on what is to be captured (e.g., proteins, metabolites, small molecules), different capture molecules may be bound on the removable sample material collector and/or different regions of the removable sample material collector.

For example, for mRNA capture and analysis, poly(dT)s that specifically bind the poly (A) tails of the mRNA may be immobilized on the removable sample material collector or regions of the removable sample material collector (e.g., corresponding to specific sample regions). The spatial information may be preserved by keying the removable sample material collector to match with a unique alignment with the sample regions and/or nanostraw membrane. Another way to preserve the spatial information is to add positional barcodes into the DNA-poly(dT)-capture molecules. Then mRNA can be converted to cDNA, which can be sequenced by standard bulk methods. smFISH or similar imaging methods may be used to detect a smaller number of mRNAs with single molecule resolution and with preserved spatial resolution.

FIG. 17b shows another variation of an apparatus as described herein. In any of these apparatuses, the bottom electrode 1717 for electroporation can be placed on the bottom of the nanostraw membrane, as shown in FIG. 17b, or, if the removable sample material collector is ionically conducting, the bottom electrolyte can extend on both sides of the capturing removable sample material collector, and the electrode can be placed underneath the removable sample material collector, as shown in FIG. 17a. In FIG. 17A, the removable sample material collector 1703' is supported by a second surface 1703. The top electrode 1709 in both cases is above the nanostraw substrate 1723.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of nondestructive sampling of intracellular sample material from within a cell, the method comprising:
    applying a voltage between an upper electrode and a lower electrode through a nanostraw to open one or more pores in a portion of the cell membrane extending over an opening of the nanostraw;
    capturing a sample material released from within the cell and into the nanostraw in a sample collector beneath the nanostraw; and
    stopping the application of voltage between the upper and lower electrodes and allowing the cell membrane to recover before more than 15% of the sample material within the cell is released.

2. The method of claim 1, wherein applying comprises applying a pulsed voltage of between 1 and 100 V between the upper electrode and the lower electrode through a nanostraw.

3. The method of claim 1, wherein capturing the sample comprises immobilizing the sample material onto a capture substrate.

4. The method of claim 1, wherein stopping the application comprises stopping the application of a train of pulses of between 1 and 100 V having a pulse width of between about 10 microseconds and 50 milliseconds after between 1 second and 300 seconds.

5. The method of claim 1, wherein applying the voltage comprises applying the voltage between an upper electrode and a lower electrode through the nanostraw and a plurality of additional nanostraws within a sample region, further wherein capturing the sample comprises capturing the sample material released into the nanostraw and the plurality of additional nanostraws in the sample collector.

6. The method of claim 1, further comprising repeating, after a minimum recovery time, the steps of applying the voltage between the upper and lower electrode through the nanostraw, capturing sample material, and stopping the application of voltage, wherein the minimum recovery time is longer than one hour.

7. The method of claim 6, wherein the minimum recovery time is longer than 6 hours.

8. The method of claim 1, further comprising saving a first time sample from the captured sample material and repeating, for a plurality of additional repetitions after a minimum recovery time between each repetition, the steps of: applying the voltage between the upper and lower electrode through the nanostraw, capturing sample material, and stopping the application of voltage, wherein an additional time sample is saved from the captured sample material for each repetition.

9. The method of claim 1, further comprising detecting the captured sample material captured in the sample collector.

10. The method of claim 1, further comprising quantifying the captured sample material captured in the sample collector.

11. The method of claim 1, further comprising identifying a plurality of different biomarkers from the captured sample material.

12. The method of claim 1, further comprising quantifying a plurality of different biomarkers from the captured sample material.

13. The method of claim 1, further comprising replacing a media surrounding the cell prior to applying the voltage with a buffer solution and replacing media around the cell following stopping of the application of voltage.

14. A method of nondestructive sampling of intracellular sample material from within a cell at multiple time points, the method comprising:
   applying a voltage of between 1 and 100 V between an upper electrode and a lower electrode through a nanostraw to open one or more pores in a portion of the cell membrane extending over an opening of the nanostraw;
   capturing a sample material released from within the cell and into the nanostraw in a sample collector beneath the nanostraw, wherein capturing comprises immobilizing the sample material onto a capture substrate;
   stopping the application of voltage between the upper and lower electrodes and allowing the cell membrane to recover before more than 15% of the sample material within the cell is released; and
   allowing the cell to recover for a minimum recovery time of at least 1 hour before reapplying the voltage and capturing additional sample material.

* * * * *